(12) United States Patent
van Rooij et al.

(10) Patent No.: US 9,163,235 B2
(45) Date of Patent: Oct. 20, 2015

(54) INHIBITORS OF THE MIR-15 FAMILY OF MICRO-RNAS

(71) Applicant: Miragen Therapeutics, Boulder, CO (US)

(72) Inventors: Eva van Rooij, Boulder, CO (US); Christina Dalby, Boulder, CO (US); Anita Seto, Boulder, CO (US)

(73) Assignee: MiRagen Therapeutics, Inc., Boulder, CO (US)

( * ) Notice: Subject to any disclaimer, the term of this patent is extended or adjusted under 35 U.S.C. 154(b) by 0 days.

(21) Appl. No.: 13/921,537

(22) Filed: Jun. 19, 2013

(65) Prior Publication Data

US 2013/0345288 A1 Dec. 26, 2013

Related U.S. Application Data

(60) Provisional application No. 61/662,772, filed on Jun. 21, 2012, provisional application No. 61/780,352, filed on Mar. 13, 2013.

(51) Int. Cl.
*C07H 21/04* (2006.01)
*C12N 15/113* (2010.01)

(52) U.S. Cl.
CPC ........ *C12N 15/113* (2013.01); *C12N 2310/113* (2013.01); *C12N 2310/315* (2013.01); *C12N 2310/3231* (2013.01); *C12N 2310/344* (2013.01); *C12N 2310/346* (2013.01)

(58) Field of Classification Search
None
See application file for complete search history.

(56) References Cited

U.S. PATENT DOCUMENTS

| | | | |
|---|---|---|---|
| 7,232,806 B2 | 6/2007 | Tuschl et al. | |
| 7,482,117 B2 | 1/2009 | Cargill et al. | |
| 7,582,744 B2 | 9/2009 | Manoharan et al. | |
| 7,759,319 B2 | 7/2010 | Lollo et al. | |
| 8,017,763 B2 | 9/2011 | Manoharan et al. | |
| 2005/0026169 A1 | 2/2005 | Cargill et al. | |
| 2005/0059005 A1 | 3/2005 | Tuschl et al. | |
| 2005/0075492 A1 | 4/2005 | Chen et al. | |
| 2005/0182011 A1 | 8/2005 | Olson et al. | |
| 2005/0261218 A1* | 11/2005 | Esau et al. | 514/44 |
| 2006/0058266 A1 | 3/2006 | Manoharan et al. | |
| 2006/0105360 A1 | 5/2006 | Croce et al. | |
| 2006/0165659 A1 | 7/2006 | Croce et al. | |
| 2006/0185027 A1 | 8/2006 | Bartel et al. | |
| 2006/0189557 A1 | 8/2006 | Slack et al. | |
| 2006/0247193 A1 | 11/2006 | Taira et al. | |
| 2006/0252722 A1 | 11/2006 | Lollo et al. | |
| 2007/0026403 A1 | 2/2007 | Hatzigeorgiou et al. | |
| 2007/0054287 A1 | 3/2007 | Bloch | |
| 2007/0213292 A1 | 9/2007 | Stoffel et al. | |
| 2007/0259827 A1 | 11/2007 | Aronin et al. | |
| 2007/0287179 A1 | 12/2007 | Tuschl et al. | |
| 2007/0292878 A1 | 12/2007 | Raymond | |
| 2008/0050744 A1 | 2/2008 | Brown et al. | |
| 2008/0176766 A1 | 7/2008 | Brown et al. | |
| 2008/0220423 A1 | 9/2008 | Moller et al. | |
| 2008/0287383 A1 | 11/2008 | Quay et al. | |
| 2009/0053718 A1 | 2/2009 | Naguibneva et al. | |
| 2009/0092980 A1 | 4/2009 | Arenz et al. | |
| 2009/0131356 A1 | 5/2009 | Bader et al. | |
| 2009/0143326 A1 | 6/2009 | Obad et al. | |
| 2009/0175827 A1 | 7/2009 | Byrom et al. | |
| 2009/0176723 A1 | 7/2009 | Brown et al. | |
| 2009/0214477 A1 | 8/2009 | Betz et al. | |
| 2009/0221685 A1 | 9/2009 | Esau et al. | |
| 2009/0226528 A1 | 9/2009 | Czech et al. | |
| 2009/0281167 A1 | 11/2009 | Shen et al. | |
| 2009/0286969 A1 | 11/2009 | Esau et al. | |
| 2009/0286973 A1 | 11/2009 | Manoharan et al. | |
| 2009/0291906 A1 | 11/2009 | Esau et al. | |
| 2009/0291907 A1 | 11/2009 | Esau et al. | |
| 2009/0293148 A1 | 11/2009 | Ren et al. | |
| 2009/0298916 A1 | 12/2009 | Kauppinen et al. | |
| 2009/0306181 A1 | 12/2009 | Ikeda et al. | |
| 2009/0326049 A1 | 12/2009 | Aristarkhov et al. | |
| 2010/0004320 A1* | 1/2010 | Elmen et al. | 514/44 R |

(Continued)

FOREIGN PATENT DOCUMENTS

CN 101426912 5/2009
EP 1627925 2/2006

(Continued)

OTHER PUBLICATIONS

Examination Report for Chinese Application No. 200880124495.1, issued Nov. 14, 2011 (English Translation).

(Continued)

*Primary Examiner* — Kimberly Chong
(74) *Attorney, Agent, or Firm* — Cooley LLP

(57) ABSTRACT

The invention provides chemically modified oligonucleotides capable of inhibiting the expression (e.g., abundance) of miR-15 family miRNAs, including miR-15a, miR-15b, miR-16, miR-195, miR-424, and miR-497. The invention provides in some embodiments, oligonucleotides capable of inhibiting, in a specific fashion, the expression or abundance of each of miR-15a, miR-15b, miR-16, miR-195, miR-424, and miR-497. The invention further provides pharmaceutical compositions comprising the oligonucleotides, and methods of treating patients having conditions or disorders relating to or involving a miR-15 family miRNA, such as a cardiovascular condition. In various embodiments, the oligonucleotides provide advantages in one or more of potency, efficiency of delivery, target specificity, toxicity, and/or stability.

17 Claims, 25 Drawing Sheets

(56) References Cited

U.S. PATENT DOCUMENTS

| | | |
|---|---|---|
| 2010/0029003 A1 | 2/2010 | Bartel et al. |
| 2010/0069471 A1 | 3/2010 | Manoharan et al. |
| 2010/0087512 A1 | 4/2010 | Tuschl et al. |
| 2010/0087513 A1 | 4/2010 | Tuschl et al. |
| 2010/0093837 A1 | 4/2010 | Tuschl et al. |
| 2010/0099748 A1 | 4/2010 | Tuschl et al. |
| 2010/0113284 A1 | 5/2010 | Aristarkhov et al. |
| 2010/0113561 A1 | 5/2010 | Tuschl et al. |
| 2010/0298410 A1 | 11/2010 | Obad et al. |
| 2010/0317713 A1 | 12/2010 | Olson et al. |
| 2012/0148664 A1 | 6/2012 | Dalby et al. |
| 2014/0066491 A1 | 3/2014 | Dalby et al. |

FOREIGN PATENT DOCUMENTS

| | | |
|---|---|---|
| EP | 1676914 | 7/2006 |
| EP | 1777301 | 4/2007 |
| EP | 1959012 | 8/2008 |
| EP | 2105145 | 9/2009 |
| EP | 2113567 | 11/2009 |
| JP | 2006-506469 | 2/2006 |
| JP | 2006-519008 | 8/2006 |
| JP | 2006-292367 | 10/2006 |
| WO | WO 03/029459 | 4/2003 |
| WO | WO 03/093441 | 11/2003 |
| WO | WO 2004/043387 | 5/2004 |
| WO | WO 2004/076622 | 9/2004 |
| WO | WO 2005/013901 | 2/2005 |
| WO | WO 2005/017145 | 2/2005 |
| WO | WO 2005/040419 | 5/2005 |
| WO | WO 2005/056797 | 6/2005 |
| WO | WO 2005/078096 | 8/2005 |
| WO | WO 2005/078139 | 8/2005 |
| WO | WO 2005/097205 | 10/2005 |
| WO | WO 2005/098029 | 10/2005 |
| WO | WO 2005/118806 | 12/2005 |
| WO | WO 2006/020768 | 2/2006 |
| WO | WO 2006/048553 | 5/2006 |
| WO | WO 2006/063356 | 6/2006 |
| WO | WO 2006/071884 | 7/2006 |
| WO | WO 2006/108473 | 10/2006 |
| WO | WO 2006/111512 | 10/2006 |
| WO | WO 2006/133022 | 12/2006 |
| WO | WO 2006/137941 | 12/2006 |
| WO | WO 2007/000668 | 1/2007 |
| WO | WO 2007/021896 | 2/2007 |
| WO | WO 2007/033023 | 3/2007 |
| WO | WO 2007/044362 | 4/2007 |
| WO | WO 2007/053184 | 5/2007 |
| WO | WO 2007/056826 | 5/2007 |
| WO | WO 2007/087451 | 8/2007 |
| WO | WO 2007/089607 | 8/2007 |
| WO | WO 2007/090073 | 8/2007 |
| WO | WO 2007/092181 | 8/2007 |
| WO | WO 2007/092182 | 8/2007 |
| WO | WO 2007/095387 | 8/2007 |
| WO | WO 2007/103808 | 9/2007 |
| WO | WO 2007/112754 | 10/2007 |
| WO | WO 2007/147067 | 12/2007 |
| WO | WO 2007/147409 | 12/2007 |
| WO | WO 2008/024499 | 2/2008 |
| WO | WO 2008/036776 | 3/2008 |
| WO | WO 2008/042231 | 4/2008 |
| WO | WO 2008/043521 | 4/2008 |
| WO | WO 2008/061537 | 5/2008 |
| WO | WO 2008/073920 | 6/2008 |
| WO | WO 2008/073921 | 6/2008 |
| WO | WO 2008/073922 | 6/2008 |
| WO | WO 2008/073923 | 6/2008 |
| WO | WO 2008/074328 | 6/2008 |
| WO | WO 2008/085797 | 7/2008 |
| WO | WO 2008/112226 | 9/2008 |
| WO | WO 2008/116267 | 10/2008 |
| WO | WO 2008/147430 | 12/2008 |
| WO | WO 2008/147839 | 12/2008 |
| WO | WO 2009/012263 | 1/2009 |
| WO | WO 2009/012468 | 1/2009 |
| WO | WO 2009/043353 | 4/2009 |
| WO | WO 2009/044895 | 4/2009 |
| WO | WO 2009/058818 | 5/2009 |
| WO | WO 2009/062169 | 5/2009 |
| WO | WO 2009/121031 | 10/2009 |
| WO | WO 2009/149182 | 12/2009 |
| WO | WO 2010/036939 | 4/2010 |
| WO | WO 2010/048585 | 4/2010 |
| WO | WO 2010/126355 | 11/2010 |

OTHER PUBLICATIONS

Supplementary European Search Report and Written Opinion for European Application No. 08847645.2, mailed Jan. 27, 2012.
International Search Report and Written Opinion for International Application No. PCT/US2008/083020, mailed May 13, 2009.
Supplementary European Search Report and Written Opinion for European Application No. 10786712.9, mailed Sep. 18, 2013.
International Search Report for International Application No. PCT/US2010/037821, mailed Sep. 8, 2010.
International Preliminary Report on Patentability for International Application No. PCT/US2010/037821, dated Dec. 12, 2011.
International Search Report and Written Opinion for International Application No. PCT/US2013/046960, mailed Nov. 15, 2013.
Chien, K. R., "MicroRNAs and the tell-tale heart," Nature, 447:389-390 (2007).
Elayadi et al., "Implications of high-affinity hybridization by locked nucleic acid oligomers for inhibition of human telomerase," Biochemistry, 41: 9973-9981 (2002).
Hullinger, T. G. et al., "Inhibition of miR-15 Protects Against Cardiac Ischemic Injury," Circ. Res., 110:71-81 (2012).
Joglekar, M. V. et al., "MicroRNA profiling of developing and regenerating pancreas reveal posttranscriptional regulation of neurogenin3," Developmental Biology, 311(2):603-612 (2007).
Lagos-Quintana, M. et al., "Identification of tissue-specific microRNAs from mouse," Current Biology, 12:735-739 (2002).
Lagos-Quintana, M. et al., "New microRNAs from mouse and human," RNA, 9:175-179 (2003).
Landgraf, P. et al., "A mammalian microRNA expression atlas based on small RNA library sequencing," Table S12. Human mature miRNA profile table, Cell, 129:1401-1414 (2007), 15 pages.
Landgraf, P. et al., "A mammalian microRNA expression atlas based on small RNA library sequencing," Cell, 129:1401-1414 (2007).
Ping, G. et al., "The Study and Use of Antisense Oligonucleotide Technique in Cardiovascular Diseases," Chinese Journal of Clinical Pharmacology and Therapeutics, 11(3):241-245 (2006).
Sempere, L. F. et al., "Expression profiling of mammalian microRNAs uncovers a subset of brain-expressed microRNAs with possible roles in murine and human neuronal differentiation," Genome Biology, 5(3):R13 (2004).
Sproat, B. S. et al.., "Highly efficient chemical synthesis of 2'-O-methyloligoribonucleotides and tetrabiotinylated derivatives; novel probes that are resistant to degradation by RNA or DNA specific nucleases," Nucleic Acids Research, 17(9):3373-3386 (1989).
Van Rooij et al., "A signature pattern of stress-responsive microRNAs that can evoke cardiac hypertrophy and heart failure," Proc. Natl. Acad. Sci. USA, vol. 103: 18255-18260, 2006.
Van Rooij et al., "Control of stress-dependent cardiac growth and gene expression by a microRNA," Science, vol. 316: 575-579, 2007.
Van Rooij et al., "MicroRNA function during cardiac hypertrophy," Abstract and Poster from 3rd Annual Symposium of the American Heart Association Council on Basic Cardiovascular Sciences: Translation of Basic Insights Into Clinical Practice: Jul. 31-Aug. 3, 2006 Keystone Conference Center Keystone, CO.
Xia, H. et al., "MicroRNA-15b regulates cell cycle progression by targeting cyclins in glioma cells," Biochemical and Biophysical Research Communications, 380(2):205-210 (2009).
Xia, L. et al., "miR-15b and miR-16 modulate multidrug resistance by targeting BCL2 in human gastric cancer cells," International Journal of Cancer, 123(2):372-379 (2008).

* cited by examiner

FIGURE 6B

| Based on real time assay | | | | |
|---|---|---|---|---|
| | miR family member | | | |
| M# | 15a | 15b | 16 | 195 |
| 11225 | - | - | - | - |
| 11220 | ++ | ++ | ++ | ++ |
| 11221 | + | ++ | ++ | ++ |
| 11222 | - | - | + | ++ |
| 10591 | - | - | - | - |
| 10670 | + | + | - | - |
| 11211 | + | ++ | ++ | ++ |
| 11213 | - | + | ++ | ++ |
| 11214 | + | ++ | ++ | ++ |
| 11215 | - | ++ | ++ | ++ |

++ is less than 50% relative detection
+ is between 50 to 90% relative detection
- is detectable inhibition

FIGURE 8B

| Based on dual luciferase assay | | | | | |
|---|---|---|---|---|---|
| | | miR family member | | | |
| M# | 15a | 15b | 16 | 195 | |
| 11225 | - | - | - | ++ | |
| 11220 | ++ | ++ | ++ | ++ | |
| 11221 | ++ | ++ | ++ | - | |
| 11222 | ++ | + | + | - | |
| 10591 | - | - | - | - | |
| 10670 | ++ | + | ++ | - | |
| 11211 | ++ | ++ | ++ | ++ | |
| 11213 | ++ | ++ | ++ | ++ | |
| 11214 | + | ++ | + | - | |
| 11215 | + | + | + | ++ | |

++ is more than 50% derepression in the window between plasmid alone and psi check 2
+ is less than 50% derepression, but above "1"
- is no derepression measured

* p-value < 0.01 compared to saline

INHIBITORS OF THE MIR-15 FAMILY OF MICRO-RNAS

RELATED APPLICATIONS

This application claims priority to and the benefit of U.S. Provisional Application No. 61/662,772, filed Jun. 21, 2012, and U.S. Provisional Application No. 61/780,352, filed Mar. 13, 2013, each of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG-037_02US_SeqList_ST25.txt, date recorded: Jun. 19, 2013, file size 10 kilobytes).

FIELD OF THE INVENTION

The present invention relates to chemical motifs for microRNA (miRNA or miR) inhibitors. More particularly, the present invention relates to chemically modified oligonucleotides that target one or more miR-15 family members and having advantages in potency, efficiency of delivery, target specificity, stability, and/or toxicity when administered to a patient.

BACKGROUND

MicroRNAs (miRs) have been implicated in a number of biological processes including regulation and maintenance of cardiac function (see, E. Van Rooij et al., *J. Clin. Invest.* 117(9): 2369-2376 (2007); K. Chien, *Nature* 447: 389-390 (2007)). Therefore, miRs represent a relatively new class of therapeutic targets for conditions such as cardiac hypertrophy, myocardial infarction, heart failure, vascular damage, and pathologic cardiac fibrosis, among others. miRs are small, non-protein coding RNAs of about 18 to about 25 nucleotides in length, and act as repressors of target mRNAs by promoting their degradation, when their sequences are perfectly complementary, or by inhibiting translation, when their sequences contain mismatches. The mechanism involves incorporation of the mature miRNA strand into the RNA-induced silencing complex (RISC), where it associates with its target RNAs by base-pair complementarity.

miRNA function may be targeted therapeutically by antisense polynucleotides or by polynucleotides that mimic miRNA function ("miRNA mimetic"). However, targeting miRNAs therapeutically with oligonucleotide-based agents poses several challenges, including RNA-binding affinity and specificity, efficiency of cellular uptake, and nuclease resistance. For example, when polynucleotides are introduced into intact cells they are attacked and degraded by nucleases leading to a loss of activity. While polynucleotide analogues have been prepared in an attempt to avoid their degradation, e.g. by means of 2' substitutions (B. Sproat et al., *Nucleic Acids Research* 17: 3373-3386, (1989)), the modifications often affect the polynucleotide's potency for its intended biological action. Such reduced potency, in each case, may be due to an inability of the modified polynucleotide to form a stable duplex with the target RNA and/or a loss of interaction with the cellular machinery. Other modifications include the use of locked nucleic acid, which has the potential to improve RNA-binding affinity (see, R. Veedu et al., *RNA Biology* 6(3): 321-323 (2009)).

Oligonucleotide chemistry patterns or motifs for miRNA inhibitors have the potential to improve the delivery, stability, potency, specificity, and/or toxicity profile of the inhibitors, and such are needed for effectively targeting miRNA function in a therapeutic context.

SUMMARY OF THE INVENTION

The present invention provides chemically modified oligonucleotides capable for reducing or inhibiting the activity of one or more miR-15 family members including miR-15a, miR-15b, miR-16, miR-195, miR-424, and miR-497. The invention further provides pharmaceutical compositions comprising the oligonucleotides, and methods of treating subjects having conditions or disorders relating to, or involving, one or more miR-15 family members. In various embodiments, the disclosed oligonucleotides provide advantages in one or more of potency, efficiency of delivery, target specificity, toxicity, and/or stability.

In one aspect, the invention provides a chemically modified oligonucleotide capable of reducing or inhibiting the activity of one or more miR-15 family members. The activity or potency of the oligonucleotide may be determined in vitro and/or in vivo. For example, the oligonucleotide may significantly inhibit (e.g., about 50% inhibition) the activity of one or more miR-15 family members (as determined, for example, in a two-step real time PCR assay or a dual luciferase assay) at a concentration of about 50 nM or less, or in other embodiments, about 40 nM or less, about 20 nM or less, or about 10 nM or less. Alternatively, or in addition, the activity of the oligonucleotide may be determined in a suitable mouse or rat model, or non-human primate model, where inhibition (e.g., by at least about 50%) of one or more miR-15 family members is observed at a dose of about 50 mg/kg or less, such as about 25 mg/kg or less, about 10 mg/kg or less, or about 5 mg/kg or less. Exemplary markers for determining target de-repression are described herein. In these embodiments, the oligonucleotide may be dosed subcutaneously or intravenously (and as described herein), and may be formulated in an aqueous preparation (e.g., saline).

The oligonucleotide comprises the nucleotide sequence 5'-GTGCTGCT-3' and is substantially complementary to a nucleotide sequence of one or more miR-15 family members. The oligonucleotide further contains at least one locked nucleotide. In an embodiment, the oligonucleotide contains at least eight locked nucleotides. The locked nucleotides may have a 2' to 4' bridge structure as described in WO 2012/083005, which is incorporated herein in its entirety. For example, the locked nucleotide may have a 2' to 4' bridge comprising an ethylene or methylene group. In another example, the locked nucleotide may have a 2' to 4' methylene bridge.

Generally, the length of the oligonucleotide and number and position of locked nucleotides is such that the oligonucleotide reduces the activity of one or more miR-15 family members at an oligonucleotide concentration of about 50 nM or less in an in vitro real time PCR assay or a luciferase assay, or at a dose of about 25 mg/kg or less in a suitable rodent model or non-human primate model as described herein. In an embodiment, the oligonucleotide is from about 8 to about 18 nucleotides in length. In another embodiment, the oligonucleotide is from about 12 to about 17 nucleotides in length.

In an exemplary embodiment, the oligonucleotide is about 16 nucleotides in length. The oligonucleotide may comprise or consist essentially of a nucleotide sequence selected from 5'-ACCATTATGTGCTGCT-3'(SEQ ID NO. 1), 5'-ACCATGATGTGCTGCT-3'(SEQ ID NO. 2), 5'-ATATTTACGTGCTGCT-3'(SEQ ID NO. 3), and 5'-ATATTTCTGTGCTGCT-3'(SEQ ID NO. 4). The oligonucleotide may include nine locked nucleotides and seven non-locked nucleotides. The pattern of locked nucleotides may be such that at least positions 1, 5, 8, 10, and 16 are locked nucleotides.

In another exemplary embodiment, the oligonucleotide is about 12 nucleotides in length. The oligonucleotide may comprise or consist essentially of a nucleotide sequence selected from 5'-TTATGTGCTGCT-3'(SEQ ID NO. 5), 5'-TTACGTGCTGCT-3'(SEQ ID NO. 6), 5'-TTCTGTGCTGCT-3'(SEQ ID NO. 7), 5'-TTCCGTGCTGCT-3'(SEQ ID NO. 8), 5'-TGATGTGCTGCT-3'(SEQ ID NO. 9), 5'-TGACGTGCTGCT-3'(SEQ ID NO. 10), 5'-TGCTGTGCTGCT-3'(SEQ ID NO. 11), and 5'-TGCCGTGCTGCT-3'(SEQ ID NO. 12). The oligonucleotide may include eight locked nucleotides and four non-locked nucleotides. The pattern of locked nucleotides may be such that at least positions 1, 4, 9, and 12 are locked nucleotides.

In yet another exemplary embodiment, the oligonucleotide is about 8 nucleotides in length. The oligonucleotide may consist essentially of, or consists of the nucleotide sequence 5'-GTGCTGCT-3', where all or substantially all (e.g., at least about 6 or at least about 7) are locked nucleotides.

In various embodiments, the region complementary to the seed region of the one or more miR-15 family members comprises at least about four locked nucleotides. In another embodiment, the oligonucleotide does not contain a stretch of nucleotides with more than three contiguous non-locked nucleotides and/or more than three contiguous locked nucleotides.

With respect to non-locked nucleotides, the nucleotide may contain a 2' modification with respect to a 2' hydroxyl. In some embodiments, the 2' modification may be independently selected from deoxy, O-alkyl, O-methyl, halo, and fluoro. For example, the 2' modification may be deoxy. In an embodiment, all the non-locked nucleotides in the oligonucleotide are 2' deoxy.

The oligonucleotide may also contain one or more phosphorothioate linkages. For example, the oligonucleotide may be fully phosphorothioate-linked or may contain about half or ¾ phosphorothioate linkages.

Exemplary oligonucleotide inhibitors are shown in Table 1.

In other embodiments, the oligonucleotide may contain a 5' and or a 3' cap structure. In yet another embodiment, the oligonucleotide may further include a pendent lipophilic group.

In another aspect, the invention provides pharmaceutical compositions and formulations comprising the oligonucleotides of the invention, which may involve incorporation of the oligonucleotide within a variety of macromolecular assemblies, micelle, or liposome compositions for cellular delivery. In certain embodiments, the oligonucleotides are formulated for conventional intravenous, subcutaneous, or intramuscular dosing. Such formulations may be conventional aqueous preparations, such as formulation in saline. In certain embodiments, the compositions are suitable or formulated for intradermal, subcutaneous, intramuscular, intraperitoneal or intravenous injection, or by direct injection into target tissue (e.g., cardiac tissue).

In still other aspects, the invention provides a method for delivering the oligonucleotide and the pharmaceutical composition to mammalian cells either in vitro or ex vivo, e.g., for treating, ameliorating, or preventing the progression of a condition in a mammalian subject. The method may comprise administering the oligonucleotide or composition comprising the same to a population of target cells or a mammalian subject at a dose effective for target de-repression of Pim1. The subject may have a condition associated with, mediated by, or resulting from, the expression of one or more miR-15 family members. Such conditions include, for example, cardiac hypertrophy, myocardial infarction, heart failure (e.g., congestive heart failure), ischemia, ischemia reperfusion injury, vascular damage, restenosis, pathologic cardiac fibrosis, or conditions associated with cardiac transplantation. Thus, the invention provides a use of the modified oligonucleotides and compositions for treating such conditions, and for the preparation of medicaments for such treatments.

Other aspects and embodiments of the invention will be apparent from the following detailed description of the invention.

DESCRIPTION OF THE FIGURES

FIG. 6. FIG. 6B is a chart summarizing the efficacy of each miR-15 inhibitor.

FIG. 8. FIG. 8B is a chart summarizing the efficacy of each miR-15 inhibitor.

FIG. 9. Efficacy of a panel of miR-15 inhibitors on target gene de-repression.

FIG. 10 shows that delivery of a single dose (25 mg/kg) of M-11215 induces potent silencing of miR-15 targets in mice as early as 24 hours post injection.

FIG. 11 shows that M-11214 elicits target gene de-repression that is specific to the miR-15 family (p-value: 0.01). The p-value for enrichment was calculated using a hypergeometric distribution function.

FIG. 12. Efficacy of a panel of miR-15 inhibitors on target gene de-repression in rats.

FIG. 13 shows that a single dose of miR-15 inhibitors (25 mg/kg) induces target gene de-repression in a rat model of ischemia-reperfusion injury (n=4; p-value <0.05 v. baseline). The p-value was calculated using ANOVA Newman-Keuls post test. Baseline represents non-infarcted controls. IR/Saline represents saline treated controls. M-10591 is a non-targeting control oligonucleotide.

FIG. 14 shows the effect of a single dose of miR-15 inhibitors (25 mg/kg) on the expression of various inflammatory markers in a rat model of ischemia-reperfusion injury (n=4). Baseline represents non-infarcted controls. IR/Saline represents saline treated controls. M-10591 is a non-targeting control oligonucleotide.

FIG. 15. Efficacy of miR-15 inhibitors on myocardial infarction in a rat stress model.

FIG. 16 shows the effects of miR-15 inhibitors on the ejection fraction in a rat model of ischemia-reperfusion injury. AMC represents age matched controls without injury. IR/Saline represents saline treated controls.

DETAILED DESCRIPTION OF THE INVENTION

Figure 1:
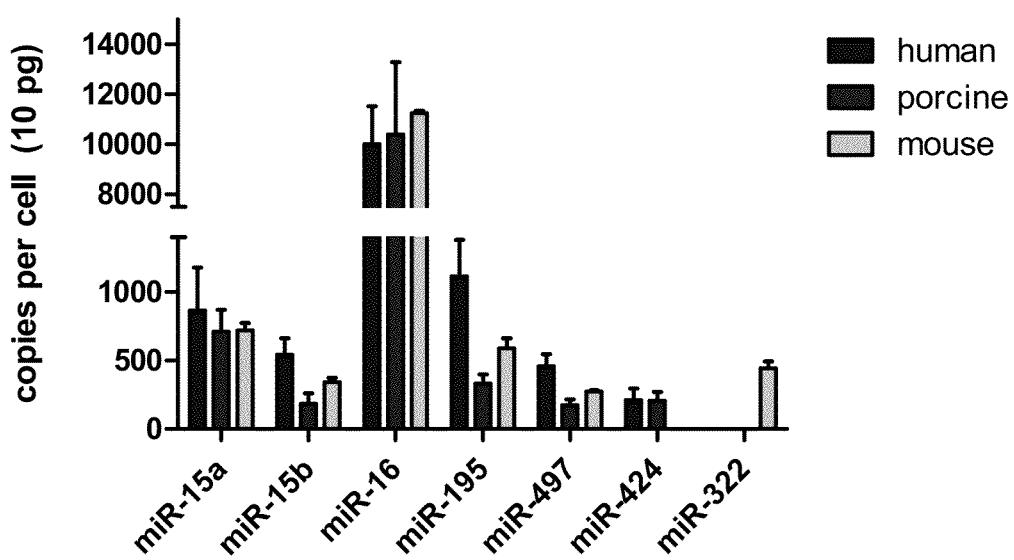
FIG. 1. Abundance of miR-15 family members in cardiocytes. MicroRNA copy numbers per cell are measured by real-time PCR analysis and normalized to a commercially available standard (Ambion).

The invention provides chemically modified oligonucleotides capable of inhibiting the expression (e.g., abundance) of miR-15 family miRNAs, including miR-15a, miR-15b, miR-16, miR-195, miR-424, and miR-497. The invention provides in some embodiments, oligonucleotides capable of inhibiting, in a specific fashion, the expression or abundance of each of miR-15a, miR-15b, miR-16, miR-195, miR-424, and miR-497. The invention further provides pharmaceutical compositions comprising the oligonucleotides, and methods of treating patients having conditions or disorders relating to or involving a miR-15 family miRNA, such as a various cardiovascular conditions. In various embodiments, the oligonucleotides provide advantages in one or more of potency, efficiency of delivery, target specificity, toxicity, and/or stability.

In one aspect, the invention provides an oligonucleotide capable of reducing the expression or abundance of miR-15 family miRNAs. The activity of the oligonucleotides may be determined in vitro and/or in vivo. For example, when inhibition of miR-15a, miR-15b, miR-16, miR-195, miR-424, and miR-497 activity is determined in vitro, the activity may be determined using a two-step real-time PCR assay or a dual luciferase assay as described herein. The oligonucleotide significantly inhibits such activity, as determined, for example, in the dual luciferase assay, at a concentration of about 75 nM or less, or in other embodiments, about 50 nM or less, about 40 nM or less, about 20 nM or less, or about 10 nM or less. For example, the oligonucleotide may have an IC50 for inhibition of miR-15a, miR-15b, miR-16, miR-195, miR-424, and miR-497 activity of about 50 nM or less, about 40 nM or less, about 30 nM or less, or about 20 nM or less, as determined in the dual luciferase assay.

The two-step PCR analysis, as exemplified by the commercially available TaqMan® MicroRNA Assay (Applied Biosystems), involves a quantitative PCR readout which can be inhibited at two steps by an oligonucleotide inhibitor: 1) by inhibiting the ability of the reverse transcriptase primer to elongate during cDNA synthesis; and 2) by inhibiting the ability of the PCR primer to amplify the cDNA product.

The dual luciferase assay, as exemplified by the commercially available product PsiCHECK™ (Promega), involves placement of the miR recognition site in the 3' UTR of a gene for a detectable protein (e.g., renilla luciferase). The construct is co-expressed with the target miRNA, such that inhibitor activity can be determined by change in signal. A second gene encoding a detectable protein (e.g., firefly luciferase) can be included on the same plasmid, and the ratio of signals determined as an indication of anti-miR activity.

Alternatively, or in addition, the activity of the oligonucleotide may be determined in a suitable mouse or rat model, such as those described herein, where inhibition (e.g., by at least about 50%) of a miR-15 family miRNA is observed at an oligonucleotide dose of about 50 mg/kg or less, about 25 mg/kg or less, such as about 10 mg/kg or less or about 5 mg/kg or less. In some embodiments, the activity of the oligonucleotides is determined in an animal model described in WO 2008/016924, which descriptions are hereby incorporated by reference. For example, the oligonucleotide may exhibit at least about 50% target miRNA inhibition or target de-repression at a dose of about 50 mg/kg or less, about 25 mg/kg or less, such as about 10 mg/kg or less or about 5 mg/kg or less. In such embodiments, the oligonucleotide may be dosed intravenously or subcutaneously to mice or to rat, and the oligonucleotide may be formulated in saline.

In these or other embodiments, the oligonucleotides of the invention are stable after administration, being detectable in the circulation and/or target organ for at least about three weeks, at least about four weeks, at least about five weeks, or at least about six weeks, or more, following administration. Thus, the oligonucleotides of the invention have the potential to provide for less frequent administration, lower doses, and/or longer duration of therapeutic effect.

The oligonucleotide comprises the nucleotide sequence 5'-GTGCTGCT-3' and is substantially complementary to a nucleotide sequence of human miR-15a, miR-15b, miR-16, miR-195, miR-424, and miR-497. The oligonucleotide further contains at least one locked nucleotide(s). For example, the oligonucleotide may contain at least eight or at least nine locked nucleotides. Generally, the length of the oligonucleotide and number and position of locked nucleotides is such that the oligonucleotide reduces the activity of miR-15a, miR-15b, miR-16, miR-195, miR-424, and miR-497 at an oligonucleotide concentration of about 50 nM or less in the in vitro luciferase assay, or at a dose of about 50 mg/kg or less, or about 25 mg/kg or less in a suitable mouse or rat model, each as described herein. A substantially complementary oligonucleotide may have from about 1 to about 5 mismatches (e.g., 1 or about 2 or about 3 or about 4 or about 5 mismatches)

with respect to its target sequence of miR-15a, miR-15b, miR-16, miR-195, miR-424, and miR-497.

The structure and processing of miR-15 family members including miR-15a, miR-15b, miR-16, miR-195, miR-424, and miR-497, as well as their potential for treating cardiac hypertrophy, heart failure, or myocardial infarction (among other conditions), are described in WO 2009/062169, which is hereby incorporated by reference. The pre-miRNA sequences for human miR-15 family members (e.g. stem loop sequences), which may be used for designing inhibitory miR-NAs in accordance with the invention, are listed below:

```
Human pre-miR-15a
                                          (SEQ ID NO. 13)
CCUUGGAGUA AAGUAGCAGC ACAUAAUGGU UUGUGGAUUU

UGAAAAGGUG CAGGCCAUAU UGUGCUGCCU CAAAAAUACA AGG

Human pre-miR-15b
                                          (SEQ ID NO. 14)
UUGAGGCCUU AAAGUACUGU AGCAGCACAU CAUGGUUUAC

AUGCUACAGU CAAGAUGCGA AUCAUUAUUU GCUGCUCUAG

AAAUUUAAGG AAAUUCAU

Human pre-miR-16-1
                                          (SEQ ID NO. 15)
GUCAGCAGUG CCUUAGCAGC ACGUAAAUAU UGGCGUUAAG

AUUCUAAAAU UAUCUCCAGU AUUAACUGUG CUGCUGAAGU

AAGGUUGAC

Human pre-miR-16-2
                                          (SEQ ID NO. 16)
GUUCCACUCU AGCAGCACGU AAAUAUUGGC GUAGUGAAAU

AUAUAUUAAA CACCAAUAUU ACUGUGCUGC UUUAGUGUGA C

Human pre-miR-195
                                          (SEQ ID NO. 17)
AGCUUCCCUG GCUCUAGCAG CACAGAAAUA UUGGCACAGG

GAAGCGAGUC UGCCAAUAUU GGCUGUGCUG CUCCAGGCAG

GGUGGUG

Human pre-miR-424
                                          (SEQ ID NO. 18)
CGAGGGGAUA CAGCAGCAAU UCAUGUUUUG AAGUGUUCUA

AAUGGUUCAA AACGUGAGGC GCUGCUAUAC CCCCUCGUGG

GGAAGGUAGA AGGUGGGG

Human pre-miR-497
                                          (SEQ ID NO. 19)
CCACCCCGGU CCUGCUCCCG CCCCAGCAGC ACACUGUGGU

UUGUACGGCA CUGUGGCCAC GUCCAAACCA CACUGUGGUG

UUAGAGCGAG GGUGGGGGAG GCACCGCCGA GG
```

Each of the pre-miRNA sequences for each miR-15 family member is processed into a mature sequence and a star sequence. The star sequence is processed from the other strand of the stem loop structure. The mature and star sequences for each of the miR-15 family members are given below:

```
Human mature miR-15a
                                          (SEQ ID NO. 20)
UAGCAGCACAUAAUGGUUUGUG Human miR-15a*
                                          (SEQ ID NO. 21)
CAGGCCAUAUUGUGCUGCCUCA Human mature miR-15b
                                          (SEQ ID NO. 22)
UAGCAGCACAUCAUGGUUUACA Human miR-15b*
                                          (SEQ ID NO. 23)
CGAAUCAUUAUUUGCUGCUCUA Human mature miR-16-1/miR-16-2
                                          (SEQ ID NO. 24)
UAGCAGCACGUAAAUAUUGGCG Human miR-16-1*
                                          (SEQ ID NO. 25)
CCAGUAUUAACUGUGCUGCUGA Human miR-16-2*
                                          (SEQ ID NO. 26)
CCAAUAUUACUGUGCUGCUUUA Human mature miR-195
                                          (SEQ ID NO. 27)
UAGCAGCACAGAAAUAUUGGC Human miR-195*
                                          (SEQ ID NO. 28)
CCAAUAUUGGCUGUGCUGCUCC Human mature miR-424
                                          (SEQ ID NO. 29)
CAGCAGCAAUUCAUGUUUUGAA Human miR-424*
                                          (SEQ ID NO. 30)
CAAAACGUGAGGCGCUGCUAU Human mature miR-497
                                          (SEQ ID NO. 31)
CAGCAGCACACUGUGGUUUGU Human miR-497*
                                          (SEQ ID NO. 32)
CAAACCACACUGUGGUGUUAGA
```

Although the seed region (e.g. bases spanning 2 to 8 nucleotides of mature miRNA sequence) for all family members is highly conserved (AGCAGCAC), the 3' end of the mature miRNA differs among the different family members.

It is contemplated that multiple members of the miR-15 family may be inhibited simultaneously by administering a single miR-15 inhibitor or by administering multiple inhibitors. For example, each inhibitor may target a single miR-15 family member or may target multiple miR-15 family members. In some embodiments, a single miR-15 inhibitor inhibits the expression or activity of two or more miR-15 family members. Such inhibitors include, but are not limited to, M-10670, M-11211, M-11213, M-11214, M-11215, M-11220, M-11221, and M-10222. In other embodiments, a single miR-15 inhibitor inhibits the expression or activity of three or more miR-15 family members. Such inhibitors include, but are not limited to, M-10670, M-11211, M-11213, M-11214, M-11215, M-11220, M-11221, and M-10222. In further embodiments, a single miR-15 inhibitor inhibits the expression or activity of four or more miR-15 family members. Such inhibitors may include, but are not limited to, M-11211, M-11213, M-11214, M-11215, M-11220, and M-11221.

The oligonucleotide contains one or more locked nucleic acid (LNAs) residues, or "locked nucleotides". LNAs are described, for example, in U.S. Pat. No. 6,268,490, U.S. Pat. No. 6,316,198, U.S. Pat. No. 6,403,566, U.S. Pat. No. 6,770,748, U.S. Pat. No. 6,998,484, U.S. Pat. No. 6,670,461, and U.S. Pat. No. 7,034,133, all of which are hereby incorporated by reference in their entireties. LNAs are modified nucleotides or ribonucleotides that contain an extra bridge between the 2' and 4' carbons of the ribose sugar moiety resulting in a "locked" conformation, and/or bicyclic structure. In one embodiment, the oligonucleotide contains one or more LNAs having the structure shown by structure A below. Alternatively or in addition, the oligonucleotide may contain one or more LNAs having the structure shown by structure B below. Alternatively or in addition, the oligonucleotide contains one or more LNAs having the structure shown by structure C below.

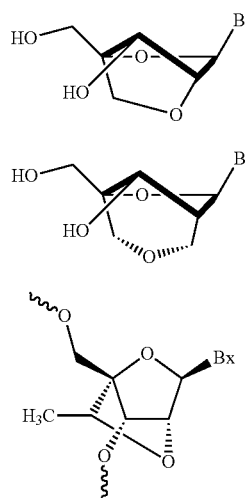

Other suitable locked nucleotides that can be incorporated in the oligonucleotides of the invention include those described in U.S. Pat. No. 6,403,566 and U.S. Pat. No. 6,833,361, both of which are hereby incorporated by reference in their entireties.

In exemplary embodiments, the locked nucleotides have a 2' to 4' methylene bridge, as shown in structure A, for example. In still other embodiments, the locked nucleotides have a bridge comprising an ethylene group, which may or may not contain an ether linkage at the 2' position.

The oligonucleotide may comprise, consist essentially of, or consist of, a full length or truncated antisense sequence of a miR-15 family member. As used herein, the term "full length" in reference to a miRNA sequence refers to the length of the mature miRNA antisense counterpart. Thus, the inhibitors described herein may be truncated or full-length, antisense, mature miRNA sequences, or may comprise these sequences in combination with other polynucleotide sequences. In certain embodiments, the chemical modification motif described herein renders full length antisense miRNA (mature) sequences unnecessary. In these embodiments, the oligonucleotide is from about 8 to about 20 nucleotides in length, or is from about 8 to about 18 nucleotides in length, or is from about 12 to about 17 nucleotides in length. The oligonucleotide in some embodiments is about 8, about 9, about 10, about 11, about 12, about 13, about 14, about 15, about 16 nucleotides in length. The truncated oligonucleotide may have a sequence that targets, by antisense inhibition, a miR-15a sequence within 5'-UAGCAGCACAUAAUGGU-3' (SEQ ID NO. 33), a miR-15b sequence within 5'-UAGCAG-CACAUCAUGGU-3' (SEQ ID NO. 34), a miR-16 sequence within 5'-UAGCAGCACGUAAAUAU-3' (SEQ ID NO. 35), a miR-195 sequence within UAGCAGCACAGAAAUAU-3' (SEQ ID NO. 36), a miR-424 sequence within 5'-CAGCAG-CAAUUCAUGUU-3' (SEQ ID NO. 37), or a miR-497 sequence within 5'-CAGCAGCACACUGUGGU-3' (SEQ ID NO. 38).

The oligonucleotide generally has a nucleotide sequence designed to target mature miR-15a, miR-15b, miR-16, miR-195, miR-424, and miR-497. The oligonucleotide may, in these or other embodiments, also or alternatively be designed to target the pre- or pri-miRNA forms. In certain embodiments, the oligonucleotide may be designed to have a sequence containing from about 1 to about 5 (e.g., about 1, about 2, about 3, or about 4) mismatches relative to the fully complementary (mature) miR-15 sequence. In certain embodiments, such antisense sequences may be incorporated into shRNAs or other RNA structures containing stem and loop portions, for example.

In an exemplary embodiment, the oligonucleotide is about 16 nucleotides in length. The oligonucleotide may comprise or consist essentially of a nucleotide sequence selected from 5'-ACCATTATGTGCTGCT-3' (SEQ ID NO. 1), 5'-ACCAT-GATGTGCTGCT-3' (SEQ ID NO. 2), 5'-ATATTTACGT-GCTGCT-3' (SEQ ID NO. 3), and 5'-ATATTTCTGTGCT-GCT-3' (SEQ ID NO. 4). The oligonucleotide may include a mix of locked and non-locked nucleotides. For example, the oligonucleotide may include nine locked nucleotides and seven non-locked nucleotides. The pattern of locked nucleotides may be such that at least positions 1, 5, 8, 10, and 16 are locked nucleotides.

In another exemplary embodiment, the oligonucleotide is about 12 nucleotides in length. The oligonucleotide may comprise or consist essentially of a nucleotide sequence selected from 5'-TTATGTGCTGCT-3'(SEQ ID NO. 5), 5'-TTACGTGCTGCT-3' (SEQ ID NO. 6), 5'-TTCTGTGCT-GCT-3' (SEQ ID NO. 7), 5'-TTCCGTGCTGCT-3' (SEQ ID NO. 8), 5'-TGATGTGCTGCT-3' (SEQ ID NO. 9), 5'-TGACGTGCTGCT-3' (SEQ ID NO. 10), 5'-TGCTGT-GCTGCT-3' (SEQ ID NO. 11), and 5'-TGCCGTGCTGCT-3' (SEQ ID NO. 12). The oligonucleotide may include a mix of locked and non-locked nucleotides. For example, the oligonucleotide may include eight locked nucleotides and four non-locked nucleotides. The pattern of locked nucleotides may be such that at least positions 1, 4, 9, and 12 are locked nucleotides.

In yet another exemplary embodiment, the oligonucleotide is about 8 nucleotides in length. The oligonucleotide may consist essentially of, or consists of the nucleotide sequence 5'-GTGCTGCT-3', where all or substantially all (e.g., at least about 6 or at least about 7) are locked nucleotides.

The oligonucleotide generally contains at least about 8 locked nucleotides, but in various embodiments is not fully comprised of locked nucleotides. Generally, the number and position of locked nucleotides is such that the oligonucleotide reduces the activity of miR-15a, miR-15b, miR-16, miR-195, miR-424, and miR-497 as determined in vitro or in vivo as described. In certain embodiments, the oligonucleotide does not contain a stretch of nucleotides with more than about four, or more than about three, contiguous non-locked nucleotides. In these or other embodiments, the region complementary to the miR-15a, miR-15b, miR-16, miR-195, miR-424, and miR-497 seed region comprises at least three or at least four locked nucleotides.

For non-locked nucleotides, the nucleotide may contain a 2' modification with respect to a 2' hydroxyl. For example, the 2' modification may be 2' deoxy. Incorporation of 2'-modified nucleotides in antisense oligonucleotides may increase both resistance of the oligonucleotides to nucleases and their thermal stability with complementary RNA. Various modifications at the 2' positions may be independently selected from those that provide increased nuclease sensitivity, without compromising molecular interactions with the RNA target or cellular machinery. Such modifications may be selected on the basis of their increased potency in vitro or in vivo. Exemplary methods for determining increased potency (e.g., IC50) for miRNA inhibition are described herein, including the dual luciferase assay and in vivo miRNA expression or target de-repression.

In some embodiments the 2' modification may be independently selected from O-alkyl (which may be substituted), halo, and deoxy (H). Substantially all, or all, nucleotide 2' positions of the non-locked nucleotides may be modified in certain embodiments, e.g., as independently selected from O-alkyl (e.g., O-methyl), halo (e.g., fluoro), deoxy (H), and amino. For example, the 2' modifications may each be independently selected from O-methyl and fluoro. In exemplary embodiments, purine nucleotides each have a 2' OMe and pyrimidine nucleotides each have a 2'-F. In certain embodiments, from one to about five 2' positions, or from about one to about three 2' positions are left unmodified (e.g., as 2' hydroxyls).

2' modifications in accordance with the invention also include small hydrocarbon substituents. The hydrocarbon substituents include alkyl, alkenyl, alkynyl, and alkoxyalkyl, where the alkyl (including the alkyl portion of alkoxy), alkenyl and alkynyl may be substituted or unsubstituted. The alkyl, alkenyl, and alkynyl may be C1 to C10 alkyl, alkenyl or alkynyl, such as C1, C2, or C3. The hydrocarbon substituents may include one or two or three non-carbon atoms, which may be independently selected from N, O, and/or S. The 2' modifications may further include the alkyl, alkenyl, and alkynyl as O-alkyl, O-alkenyl, and O-alkynyl.

Exemplary 2' modifications in accordance with the invention include 2'-O-alkyl (C1-3 alkyl, such as 2'OMe or 2'OEt), 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) substitutions.

In certain embodiments, the oligonucleotide contains at least one 2'-halo modification (e.g., in place of a 2' hydroxyl), such as 2'-fluoro, 2'-chloro, 2'-bromo, and 2'-iodo. In some embodiments, the 2' halo modification is fluoro. The oligonucleotide may contain from 1 to about 5 2'-halo modifications (e.g., fluoro), or from 1 to about 3 2'-halo modifications (e.g., fluoro). In some embodiments, the oligonucleotide contains all 2'-fluoro nucleotides at non-locked positions, or 2'-fluoro on all non-locked pyrimidine nucleotides. In certain embodiments, the 2'-fluoro groups are independently di-, tri-, or un-methylated.

The oligonucleotide may have one or more 2'-deoxy modifications (e.g., H for 2' hydroxyl), and in some embodiments, contains from about 2 to about 10 2'-deoxy modifications at non-locked positions, or contains 2' deoxy at all non-locked positions.

In exemplary embodiments, the oligonucleotide contains 2' positions modified as 2'OMe in non-locked positions. Alternatively, non-locked purine nucleotides are modified at the 2' position as 2'OMe, with non-locked pyrimidine nucleotides modified at the 2' position as 2'-fluoro.

In certain embodiments, the oligonucleotide further comprises at least one terminal modification or "cap". The cap may be a 5' and/or a 3'-cap structure. The terms "cap" or "end-cap" include chemical modifications at either terminus of the oligonucleotide (with respect to terminal ribonucleotides), and including modifications at the linkage between the last two nucleotides on the 5' end and the last two nucleotides on the 3' end. The cap structure as described herein may increase resistance of the oligonucleotide to exonucleases without compromising molecular interactions with the RNA target or cellular machinery. Such modifications may be selected on the basis of their increased potency in vitro or in vivo. The cap can be present at the 5'-terminus (5'-cap) or at the 3'-terminus (3'-cap) or can be present on both ends. In certain embodiments, the 5'- and/or 3'-cap is independently selected from phosphorothioate monophosphate, abasic residue (moiety), phosphorothioate linkage, 4'-thio nucleotide, carbocyclic nucleotide, phosphorodithioate linkage, inverted nucleotide or inverted abasic moiety (2'-3' or 3'-3'), phosphorodithioate monophosphate, and methylphosphonate moiety. The phosphorothioate or phosphorodithioate linkage(s), when part of a cap structure, are generally positioned between the two terminal nucleotides on the 5' end and the two terminal nucleotides on the 3' end.

In certain embodiments, the oligonucleotide has at least one terminal phosphorothioate monophosphate. The phosphorothioate monophosphate may support a higher potency by inhibiting the action of exonucleases. The phosphorothioate monophosphate may be at the 5' and/or 3' end of the oligonucleotide. A phosphorothioate monophosphate is defined by the following structures, where B is base, and R is a 2' modification as described above:

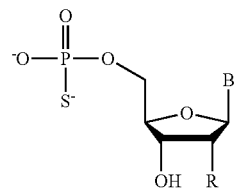 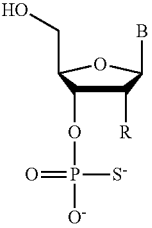

5' phosphorothioate monophosphate  3' phosphorothioate monophosphate

Where the cap structure can support the chemistry of a locked nucleotide, the cap structure may incorporate a locked nucleotide as described herein.

Phosphorothioate linkages may be present in some embodiments, such as between the last two nucleotides on the 5' and the 3' end (e.g., as part of a cap structure), or as alternating with phosphodiester bonds. In these or other embodiments, the oligonucleotide may contain at least one terminal abasic residue at either or both the 5' and 3' ends. An abasic moiety does not contain a commonly recognized purine or pyrimidine nucleotide base, such as adenosine, guanine, cytosine, uracil or thymine. Thus, such abasic moieties lack a nucleotide base or have other non-nucleotide base chemical groups at the 1' position. For example, the abasic nucleotide may be a reverse abasic nucleotide, e.g., where a reverse abasic phosphoramidite is coupled via a 5' amidite (instead of 3' amidite) resulting in a 5'-5' phosphate bond. The structure of a reverse abasic nucleoside for the 5' and the 3' end of a polynucleotide is shown below.

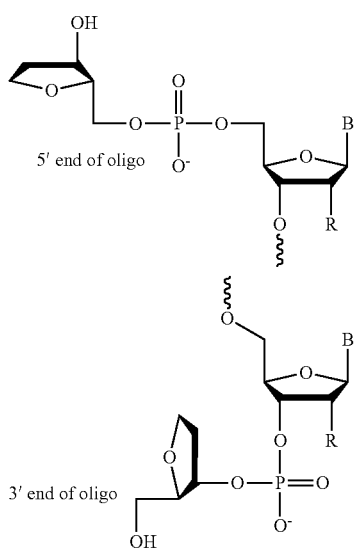

The oligonucleotide may contain one or more phosphorothioate linkages. Phosphorothioate linkages have been used to render oligonucleotides more resistant to nuclease cleavage. For example, the polynucleotide may be partially phosphorothioate-linked, for example, phosphorothioate linkages may alternate with phophodiester linkages. In certain embodiments, however, the oligonucleotide is fully phosphorothioate-linked. In other embodiments, the oligonucleotide has from about one to about five or about one to about three phosphate linkages.

In some embodiments, the nucleotide has one or more carboxamido-modified bases as described in WO 2012/061810, which is hereby incorporated by reference, including with respect to all exemplary pyrimidine carboxamido modifications disclosed therein with heterocyclic substituents.

In exemplary embodiments, the oligonucleotide has the structure of a compound listed in Table 1, below. As depicted in Table 1, a plus sign (e.g., +A) indicates a LNA base. All other bases are DNA. Each miR-15 inhibitor has a fully phosphorothioate linked backbone.

TABLE 1

Exemplary Oligonucleotides

| Compound # | Inhibitor Alias | Length | Inhibitor sequence (5' to 3') | Modification pattern | Predicted $T_m$ |
|---|---|---|---|---|---|
| M-11206 | miR15a_16_1 | 16 | ACCATTATGTGCTGCT (SEQ ID NO. 1) | +ACC+A+TT+A+TG+T+GCT+GC+T | 86 |
| M-11207 | miR15a_16_2 | 16 | ACCATTATGTGCTGCT (SEQ ID NO. 1) | +ACCA+T+TA+TG+T+GC+TG+C+T | 85 |
| M-11208 | miR15a_16_3 | 16 | ACCATTATGTGCTGCT (SEQ ID NO. 1) | +AC+CA+TT+A+TG+TG+CT+GC+T | 91 |
| M-10134 | miR15b_16_1 | 16 | ACCATGATGTGCTGCT (SEQ ID NO. 2) | +ACC+A+TG+A+TG+T+GCT+GC+T | 87 |
| M-11209 | miR15b_16_2 | 16 | ACCATGATGTGCTGCT (SEQ ID NO. 2) | +ACCA+T+GA+TG+T+GC+TG+C+T | 84 |
| M-11210 | miR15b_16_3 | 16 | ACCATGATGTGCTGCT (SEQ ID NO. 2) | +AC+CA+TG+A+TG+TG+CT+GC+T | 92 |
| M-10670 | miR16_16_1 | 16 | ATATTTACGTGCTGCT (SEQ ID NO. 3) | +ATA+T+TT+A+CG+T+GCT+GC+T | 88 |
| M-11211 | miR16_16_2 | 16 | ATATTTACGTGCTGCT (SEQ ID NO. 3) | +ATAT+T+TA+CG+T+GC+TG+C+T | 83 |
| M-11212 | miR16_16_3 | 16 | ATATTTACGTGCTGCT (SEQ ID NO. 3) | +AT+AT+TT+A+CG+TG+CT+GC+T | 92 |
| M-11213 | miR195_16_1 | 16 | ATATTTCTGTGCTGCT (SEQ ID NO. 4) | +ATA+T+TT+C+TG+T+GCT+GC+T | 83 |
| M-11214 | miR195_16_2 | 16 | ATATTTCTGTGCTGCT (SEQ ID NO. 4) | +ATAT+T+TC+TG+T+GC+TG+C+T | 85 |
| M-11215 | miR195_16_3 | 16 | ATATTTCTGTGCTGCT (SEQ ID NO. 4) | +AT+AT+TT+C+TG+TG+CT+GC+T | 87 |
| M-10564 | miR15fam_12_1 | 12 | TTATGTGCTGCT (SEQ ID NO. 5) | ++TT+A+T+CT+CC+T+CC+T | 80 |
| M-10566 | miR15fam_12_2 | 12 | TTATGTGCTGCT (SEQ ID NO. 5) | +T+TA+TG+TG+C+TG+C+T | 78 |
| M-11216 | miR15fam_12_3 | 12 | TTACGTGCTGCT (SEQ ID NO. 6) | +TT+A+C+GT+GC+T+GC+T | 83 |

TABLE 1-continued

Exemplary Oligonucleotides

| Compound # | Inhibitor Alias | Length | Inhibitor sequence (5' to 3') | Modification pattern | Predicted $T_m$ |
|---|---|---|---|---|---|
| M-10567 | miR15fam_12_4 | 12 | TTCTGTGCTGCT (SEQ ID NO. 7) | +TT+C+T+GT+GC+T+GC+T | 80 |
| M-11217 | miR15fam_12_5 | 12 | TTCTGTGCTGCT (SEQ ID NO. 7) | +T+TC+TG+TG+C+TG+C+T | 85 |
| M-11218 | miR15fam_12_6 | 12 | TTCCGTGCTGCT (SEQ ID NO. 8) | +T+TC+CG+TG+C+TG+C+T | 90 |
| M-11219 | miR15fam_12_7 | 12 | TGATGTGCTGCT (SEQ ID NO. 9) | +TG+A+T+GT+GC+T+GC+T | 81 |
| M-11220 | miR15fam_12_8 | 12 | TGATGTGCTGCT (SEQ ID NO. 9) | +T+GA+TG+TG+C+TG+C+T | 75 |
| M-11221 | miR15fam_12_9 | 12 | TGACGTGCTGCT (SEQ ID NO. 10) | +T+GA+CG+TG+C+TG+C+T | 80 |
| M-11222 | miR15fam_12_10 | 12 | TGCTGTGCTGCT (SEQ ID NO. 11) | +T+GC+TG+TG+C+TG+C+T | 82 |
| M-11223 | miR15fam_12_11 | 12 | TGCTGTGCTGCT (SEQ ID NO. 11) | +TG+C+T+GT+GC+T+GC+T | 82 |
| M-11224 | miR15fam_12_12 | 12 | TGCCGTGCTGCT (SEQ ID NO. 12) | +T+GC+CG+TG+C+TG+C+T | 86 |
| M-10113 | miR15fam_Tiny | 8 | GTGCTGCT | +G+T+G+C+T+G+C+T | 39 |

The synthesis of oligonucleotides, including modified polynucleotides, by solid phase synthesis is well known and is reviewed in *New Chemical Methods for Synthesizing Polynucleotides*. Caruthers M H, Beaucage S L, Efcavitch J W, Fisher E F, Matteucci M D, Stabinsky Y. Nucleic Acids Symp. Ser. (7):215-23, (1980).

The oligonucleotide may be incorporated within a variety of macromolecular assemblies or compositions. Such complexes for delivery may include a variety of liposomes, nanoparticles, and micelles, formulated for delivery to a patient. The complexes may include one or more fusogenic or lipophilic molecules to initiate cellular membrane penetration. Such molecules are described, for example, in U.S. Pat. No. 7,404,969 and U.S. Pat. No. 7,202,227, which are hereby incorporated by reference in their entireties. Alternatively, the oligonucleotide may further comprise a pendant lipophilic group to aid cellular delivery, such as those described in WO 2010/129672, which is hereby incorporated by reference.

The composition or formulation may employ a plurality of therapeutic oligonucleotides, including at least one described herein. For example, the composition or formulation may employ at least about 2, about 3, about 4, or about 5 miRNA inhibitors described herein.

The oligonucleotides of the invention may be formulated as a variety of pharmaceutical compositions. Pharmaceutical compositions will be prepared in a form appropriate for the intended application. Generally, this will entail preparing compositions that are essentially free of pyrogens, as well as other impurities that could be harmful to humans or animals. Exemplary delivery/formulation systems include colloidal dispersion systems, macromolecule complexes, nanocapsules, microspheres, beads, and lipid-based systems including oil-in-water emulsions, micelles, mixed micelles, and liposomes. Commercially available fat emulsions that are suitable for delivering the nucleic acids of the invention to cardiac and skeletal muscle tissues include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO 2003/093449, which are hereby incorporated by reference in their entireties.

In some embodiments, the oligonucleotide is formulated for conventional subcutaneous or intravenous administration, for example, by formulating with appropriate aqueous diluent, including sterile water and normal saline.

The pharmaceutical compositions and formulations may employ appropriate salts and buffers to render delivery vehicles stable and allow for uptake by target cells. Aqueous compositions of the present invention comprise an effective amount of the delivery vehicle comprising the inhibitor oligonucleotide (e.g. liposomes or other complexes), dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" may include one or more solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Supplementary active ingredients also can be incorporated into the compositions.

Administration or delivery of the pharmaceutical compositions according to the present invention may be via any route so long as the target tissue is available via that route. For example, administration may be by intradermal, subcutaneous, intramuscular, intraperitoneal or intravenous injection, or by direct injection into target tissue (e.g., cardiac tissue). The stability and/or potency of the oligonucleotides disclosed herein allows for convenient routes of administration, including subcutaneous, intradermal, and intramuscular. Pharmaceutical compositions comprising miRNA inhibitors may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. No. 6,416,510; U.S. Pat. No. 6,716,196; U.S. Pat. No. 6,953,466, WO 2005/082440, WO 2006/089340, U.S. Patent Publication No. 2007/0203445, U.S. Patent Publication No. 2006/0148742, and U.S. Patent Publication No. 2007/0060907, which are all hereby incorporated by reference in their entireties.

The compositions or formulations may also be administered parenterally or intraperitoneally. By way of illustration, solutions of the conjugates as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial or antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the conjugates in an appropriate amount into a solvent along with any other ingredients (for example as enumerated above) as desired. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The invention provides a method for delivering oligonucleotides to a mammalian cell (e.g., as part of a composition or formulation described herein), and methods for treating, ameliorating, or preventing the progression of a condition in a mammalian patient. The oligonucleotide or pharmaceutical composition may be contacted in vitro or in vivo with a target cell (e.g., a mammalian cell). The cell may be a heart cell.

The method generally comprises administering the oligonucleotide or composition comprising the same to a mammalian patient or population of target cells. The oligonucleotide, as already described, is a miRNA inhibitor (e.g., having a nucleotide sequence designed to inhibit expression or activity of a miR-15 family miRNA). Thus, the patient may have a condition associated with, mediated by, or resulting from, miR-15 family expression. Such conditions are described in WO 2009/062169, which is hereby incorporated by reference. These include, for example, cardiac hypertrophy, myocardial infarction, heart failure (e.g., congestive heart failure), vascular damage, ischemia, ischemia reperfusion injury, restenosis, or pathologic cardiac fibrosis as well as conditions associated with cardiac transplantation. Thus, the invention provides a use of the modified oligonucleotides and compositions of the invention for treating such conditions, and for the preparation of medicaments for such treatments.

In certain embodiments, the patient (e.g., human patient) has one or more risk factors including, for example, long standing uncontrolled hypertension, uncorrected valvular disease, chronic angina, recent myocardial infarction, congestive heart failure, congenital predisposition to heart disease and pathological hypertrophy. Alternatively or in addition, the patient may have been diagnosed as having a genetic predisposition to, for example, cardiac hypertrophy, or may have a familial history of, for example, cardiac hypertrophy.

In this aspect, administration of an inhibitor of a miR-15 family member results in the improvement of one or more symptoms of, for example, cardiac hypertrophy, heart failure, ischemia, ischemia reperfusion injury, or myocardial infarction in the subject, or in the delay in the transition from cardiac hypertrophy to heart failure. The one or more improved symptoms may be, for example, increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased left and right ventricular wall stress, decreased wall tension, increased quality of life, and decreased disease related morbidity or mortality. In addition, use of inhibitors of miR-15 family members may prevent cardiac hypertrophy and its associated symptoms from arising.

In some embodiments of the invention, an inhibitor of the miR-15 family members may be administered in combination with other therapeutic modalities. For example, a miR-15 inhibitor of the invention may be administered in conjunction with other types of therapeutic agents such as anti-hyperlipoproteinemic agents, anti-arteriosclerotic agents, anti-thrombotic/fibrinolytic agents, blood coagulants, anti-arrhythmic agents, anti-hypertensive agents, treatment agents for congestive heart failure, anti-anginal agents, anti-bacterial agents, vasodilators, hormone antagonists, iontropes, diuretics, endothelin receptor antagonists, calcium channel blockers, phosphodiesterase inhibitors, angiotensin II converting enzyme (ACE) inhibitors, cytokine blockers/inhibitors, HDAC inhibitors or a combination thereof. The combination therapy also may involve inhibiting the expression or activity of additional miRNAs involved in cardiac remodeling such as miR-499, miR-208, miR-208b and miR-21, which are described in WO 2012/083005 and WO2009/058818, the contents of which are hereby incorporated by reference. Further, a miR-15 inhibitor may be administered in conjunction with surgery. A miR-15 inhibitor may also be administered together with non-pharmacological means of treatment. For example, with respect to cardiac disorders, non-pharmacological treatment may involve reducing sodium in the diet.

In various embodiments, the pharmaceutical composition is administered by parenteral administration or by direct injection into heart tissue. The parenteral administration may be intravenous, subcutaneous, or intramuscular. In some embodiments, the composition is administered by oral, transdermal, sustained release, controlled release, delayed release, suppository, catheter, or sublingual administration. In certain embodiments, the oligonucleotide is administered at a dose of about 25 mg/kg or less, or a dose of about 10 mg/kg or less, or a dose of about 5 mg/kg or less. In these embodiments, the oligonucleotide or composition may be administered by intramuscular or subcutaneous injection, or intravenously.

In certain embodiments, the activity of miR-15a, miR-15b, miR-16, miR-195, miR-424, and miR-497 in cardiac tissue, or as determined in patient serum, is reduced or inhibited.

In an embodiment, the method of the invention may comprise administering a miR-15 family inhibitor, which may be an oligonucleotide described herein, to a population of target cells or a mammalian subject at a dose effective for target de-repression of Pim1. In a further embodiment, the present invention also provides method of regulating expression of Pim1 and other target genes such as Bcl2L2, Birc5, Gm, and Cdc2A in a cell comprising contacting the cell with a miR-15 inhibitor. In an embodiment, the expression of Pim1, Bcl2L2, Birc5, Gm, and Cdc2A are increased following administration of a miR-15 inhibitor. Expression of Pim1 and/or other markers described herein may be monitored before, during, or after treatment to determine treatment response.

In some embodiments, the methods further comprise scavenging or clearing the miRNA inhibitors following treatment. For example, an oligonucleotide having a nucleotide sequence that is complementary to the inhibitor may be administered after therapy to attenuate or stop the function of the inhibitor.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1

Abundance of miR-15 Family Members in Cardiac Tissue

The abundance of miR-15 family members in cardiac tissue was assessed by real-time PCR analysis. Specifically, total RNA was extracted from human (n=6), porcine (n=6), and mouse (n=30) cardiocytes. MicroRNA copy numbers per cell was then determined using real-time PCR and normalized to a commercially available standard (Ambion).

The results (FIG. 1) show that miR-16 is the most abundant of the miR-15 family members in cardiac tissue, with approximately 10,000 copes per cell. Other miR-15 family members including miR-15a, miR-15b, miR-195, miR-497, miR-424, and miR-322 are expressed at approximately 1,000 copies per cell. In addition, miR-322 appears to be only expressed in rodents while miR-424 expression appears to be restricted to larger animals (e.g., human and pigs).

Example 2

Identification of Gene Targets Regulated by miR-15 Family Members

A panel of miRNA inhibitors (single stranded oligonucleotides) was synthesized targeting the miR-15 family (miR-15a, miR-15b, miR-16, miR-195, miR-497, miR-424, and miR-322). The sequences and modification patterns are shown in Table 1. The panel included multiple lengths of reverse complement inhibitors ranging from 8 nucleotides to 16 nucleotides. The number of LNA modifications was varied as well as the location of the LNA modifications in the oligonucleotide.

Figure 2:
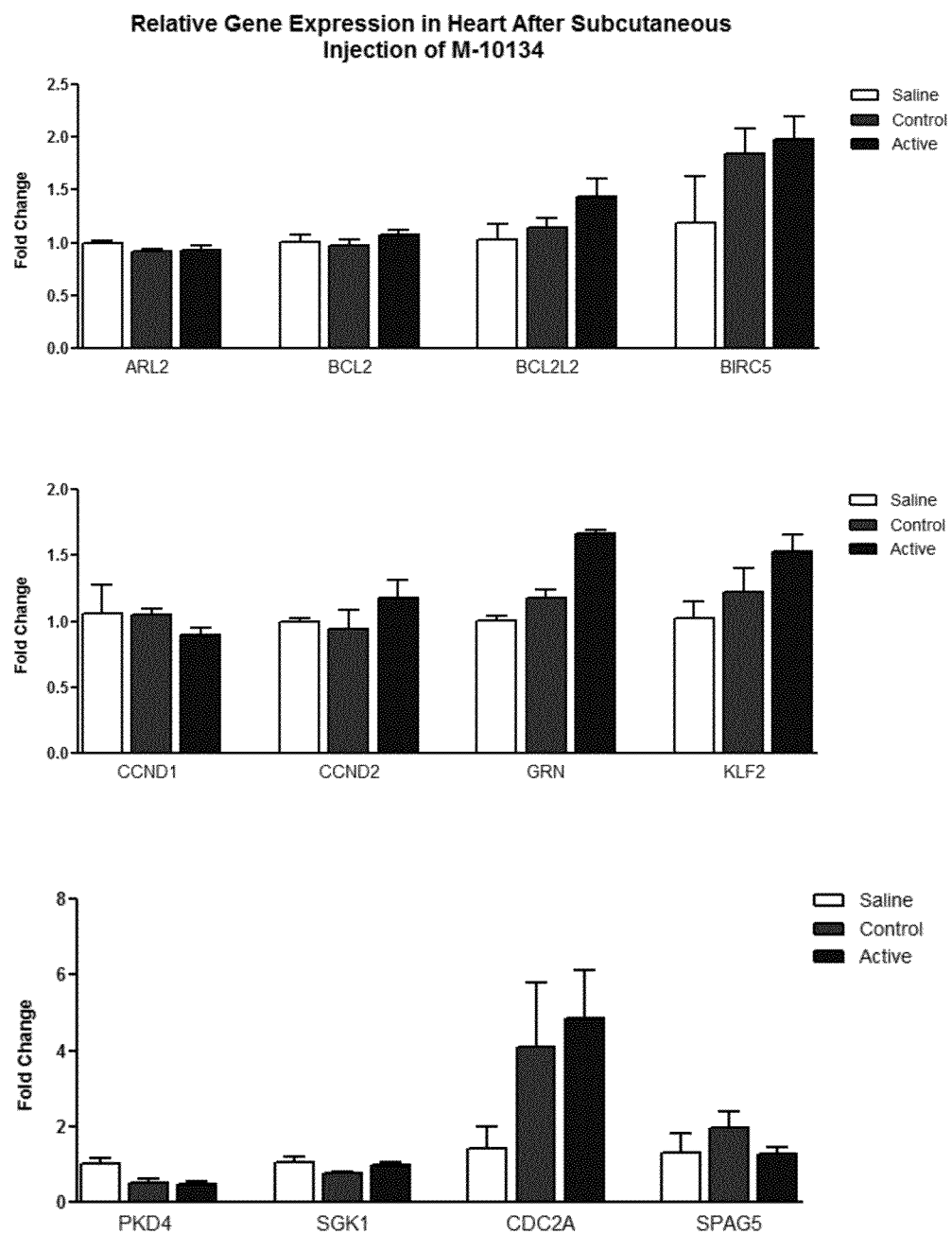
FIG. 2. miR-15 targets in cardiac tissue. Real-time PCR analysis demonstrates that subcutaneous delivery of 25 mg/kg of anti-miR15b (M-10134) induces robust changes in the expression of Bcl2L2, Birc5, Gm, and Cdc2A in mice.

Previous studies have identified potential gene targets regulated by the miR-15 family members. To identify specific miR-15 family targets in cardiac tissue, wild-type C57BL6 mice were subcutaneously injected with either saline, or 25 mg/kg of a control oligonucleotide or an anti-miR15b oligonucleotide (M-10134). Three doses were given during a treatment period of three days. Cardiac tissue was harvested at 24 hours following the last injection, and target gene expression was assessed by real-time PCR. The results (FIG. 2) show that expression of Bcl2L2, Birc5, Gm, and Cdc2A increases significantly following miR15b inhibition, suggesting that these genes are regulated by miR-15 family members in cardiac tissue.

To further verify miR-15 family targets, wild-type C57/BL6 mice were subcutaneously injected with either saline, or 2.8 mg/kg, 10 mg/kg, or 25 mg/kg of a control oligonucleotide or an anti-miR15b oligonucleotide (M-10134). Three doses were given during a treatment period of three days.

Figure 3:
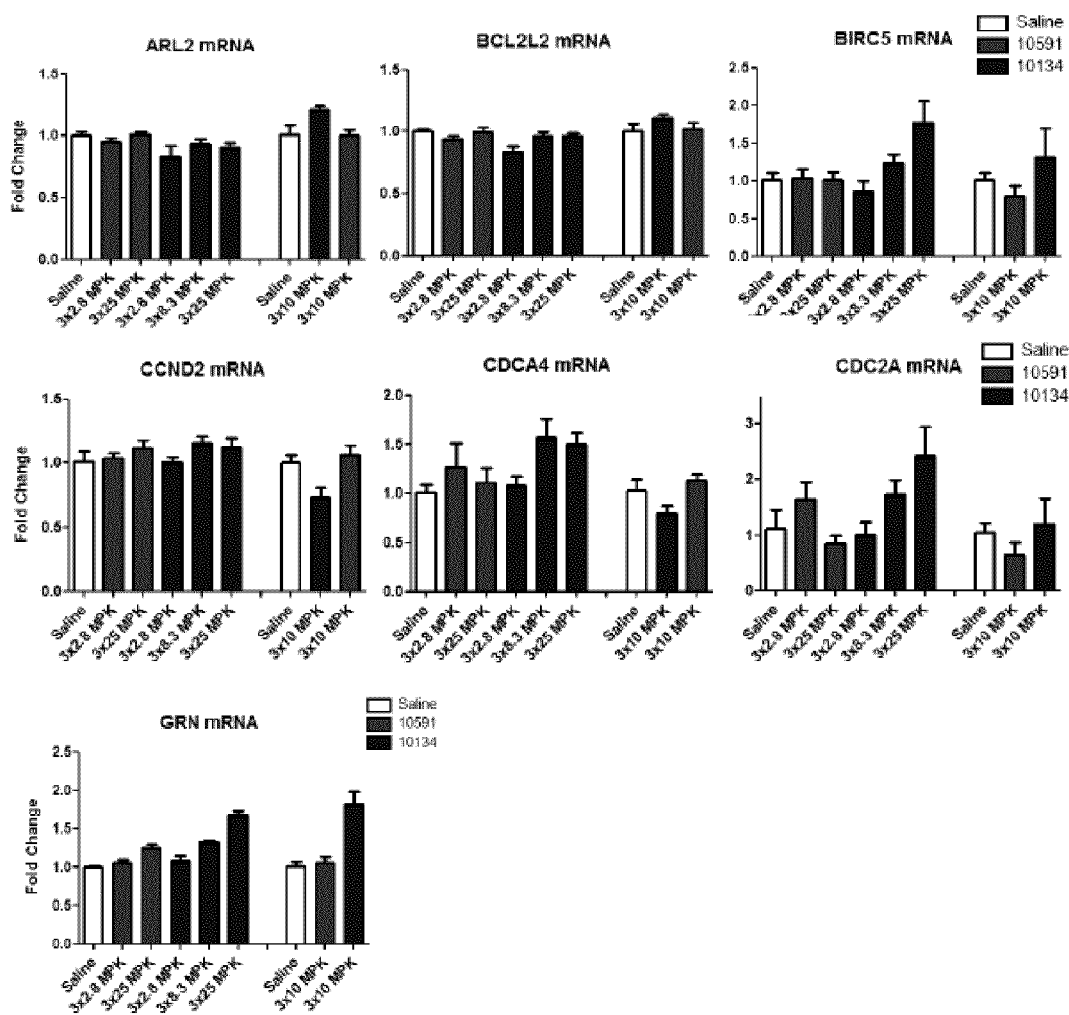
FIG. 3. Anti-miR15b (M-10134) treatment affects target gene expression in a dose-dependent manner. Real-time PCR analysis demonstrates a dose-dependent de-repression of miR-15 targets, particularly, Birc5, Gm, and Cdc2A in mice. M-10591 is a non-targeting control oligonucleotide.

Cardiac tissue was harvested at 24 hours following the last injection, and target gene expression was assessed by real-time PCR. The results (FIG. 3) show that Birc5, Cdc2A, and Gm are particularly sensitive to miR-15b inhibition. Specifically, expression of these genes increases in response to miR-15b inhibition in a dose-dependent manner.

Example 3

Activity of miRNA Inhibitors Targeting the miR-15 Family

Twenty five miRNA inhibitors (as shown in Table 1) were tested for their ability to inhibit miR-15 family members.

A. In Vivo Inhibition of miR-15 Family Members by miRNA Inhibitors

Figure 4:
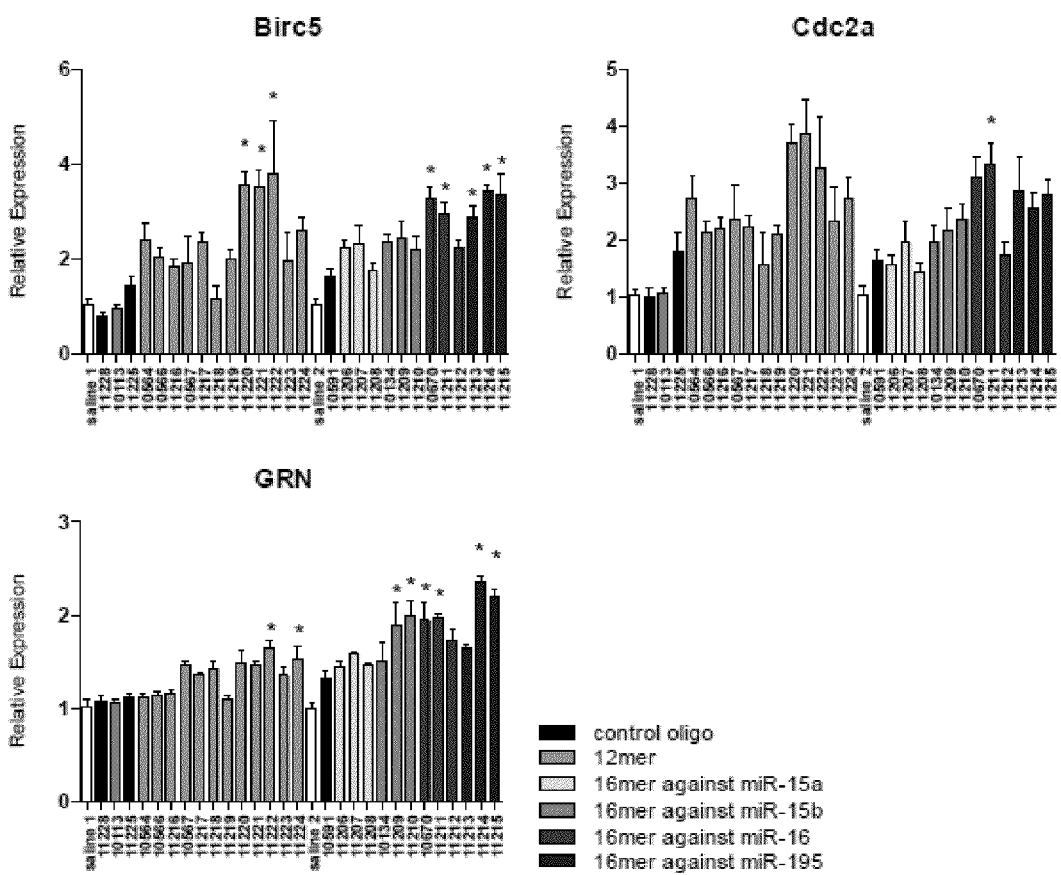
FIG. 4. Efficacy of miR-15 inhibitors against miR-15 targets measured by real-time PCR analysis. Inhibitors M-10670, M-11211, M-11213, M-11214, M-11215, M-11220, M-11221, and M-11222 appear to exert the strongest effect on miR-15 target genes in mice. Error bars depict SEM. Groups where p-value <0.001 are indicated with an asterisk.
Figure 4:
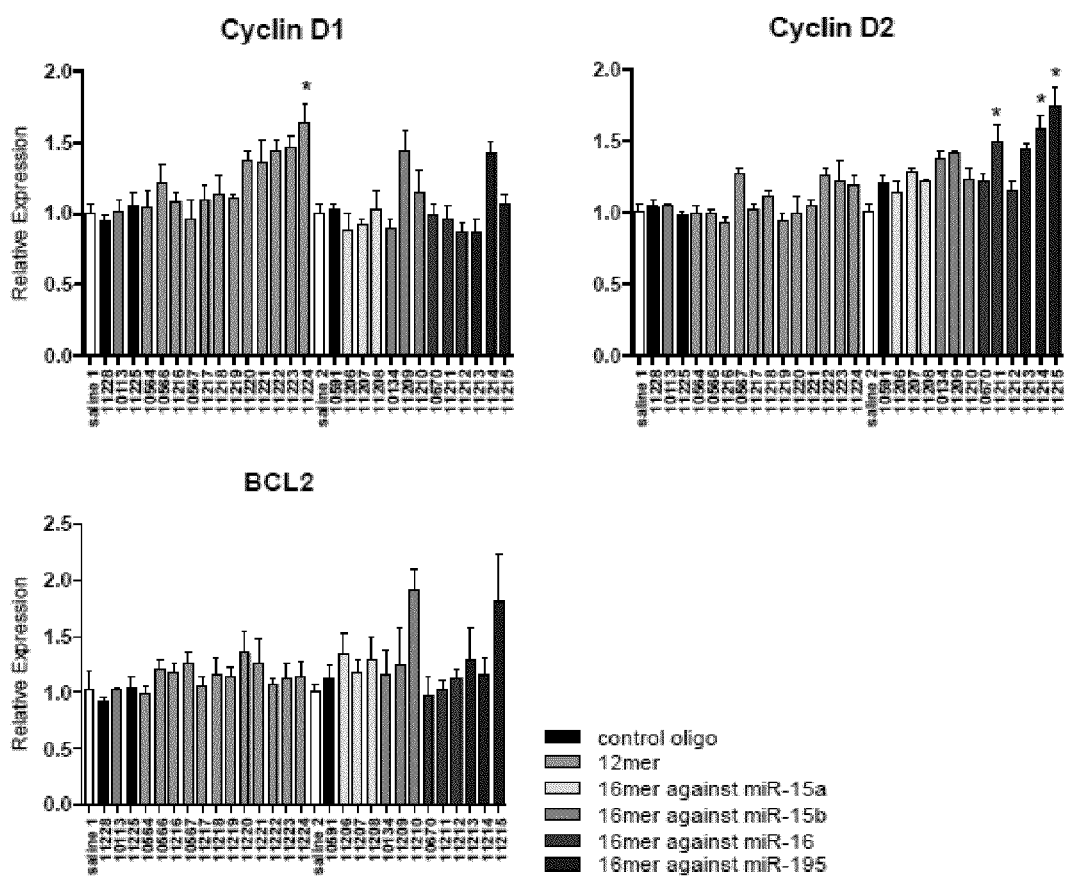
Figure 5:
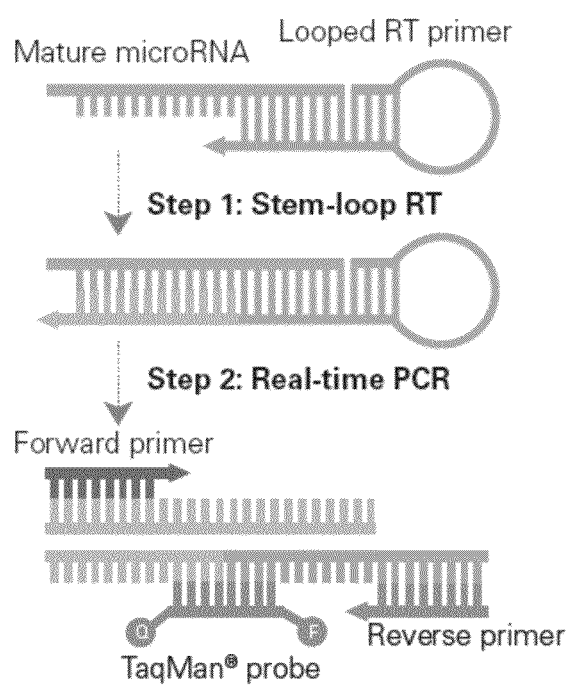
FIG. 5. The TaqMan® MicroRNA Assay (Applied Biosystems) for quantifying inhibitor activity in vitro using real-time PCR analysis.

To determine the efficacy of miR15 inhibitors on miR15 target gene expression, wild-type C57/BL6 mice were subcutaneously injected with either saline, or 25 mg/kg of a control oligonucleotide or individual anti-miR15 oligonucleotides. Three doses were given during a treatment period of three days. Cardiac tissue was harvested at 24 hours following the last injection, and target gene expression was assessed by real-time PCR. As shown in FIG. 4, the length of the miRNA inhibitor as well as LNA patterns impart distinct inhibitory activities. Particularly, inhibitors M-10670, M-11211, M-11213, M-11214, M-11215, M-11220, M-11221, M-11222 strongly affect the expression of miR-15 target genes such as Birc5, Cdc2A, Gm, CcnD1, and CcnD2. These inhibitors vary from 12 nucleotides in length to 16 nucleotides in length. Of these, the 12-mer inhibitor M-11211 appears to exhibit the most potent inhibitory activity, affecting the expression of four out of five miR-15 target genes.

Figure 6A:
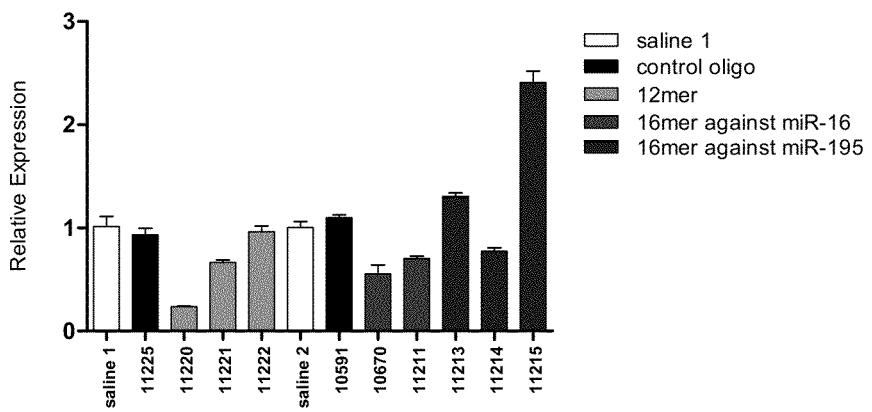
FIG. 6A shows miR-15 inhibitor efficacy measured by two-step real-time PCR analysis for miR-15a, miR-15b, miR-16, and miR-195.
Figure 6A:
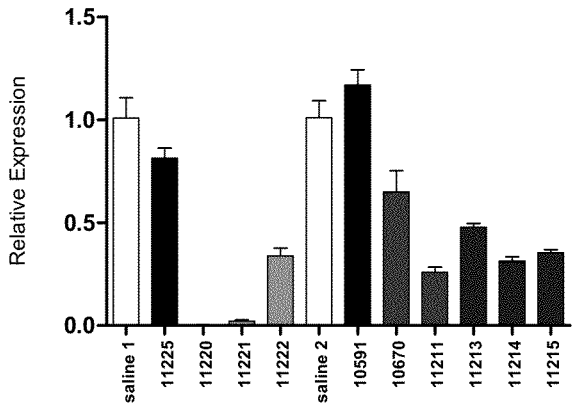
Figure 6A:
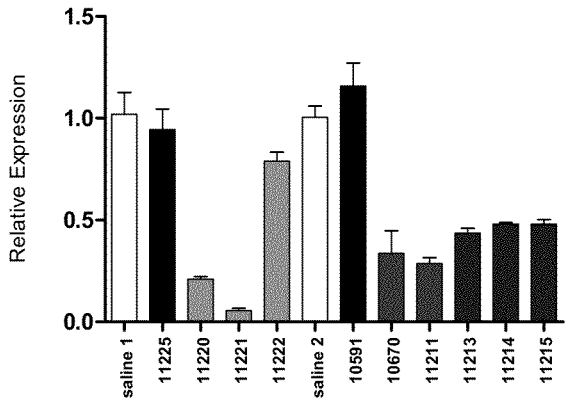
Figure 6A:
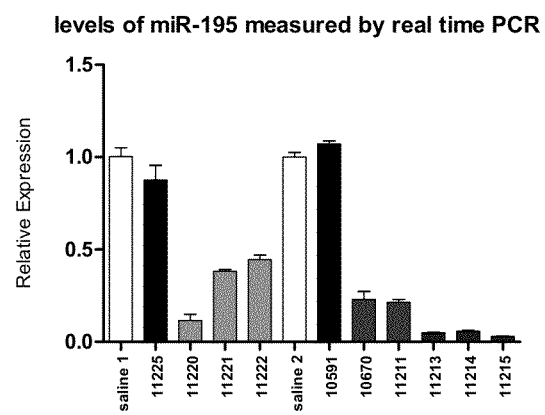
Figure 7:
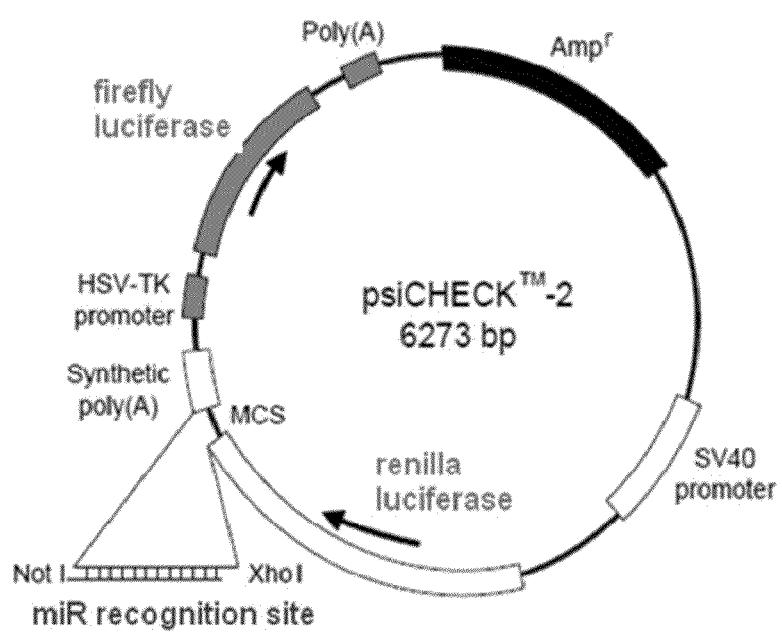
FIG. 7. The psiCHECK™-2 construct (Promega) for quantifying inhibitor activity in vitro using the dual luciferase assay.

A two-step real-time PCR assay (Applied Biosystems) was utilized to assess the ability of miRNA inhibitors to inhibit individual miR-15 family members. Specifically, the potent compounds identified previously including M-10670, M-11211, M-11213, M-11214, M-11215, M-11220, M-11221, M-11222 were tested for their effects on miR-15a, miR-15b, miR16, and miR-195 expression. Wild-type C57/BL6 mice were subcutaneously injected with either saline, or 25 mg/kg of a control oligonucleotide or anti-miR15 oligonucleotides as previously described. Three doses were given during a treatment period of three days. The results (FIGS. 6A and 6B) show that the 12-mer inhibitor M-11220 is the best inhibitor tested and inhibits all four miR-15 family members including miR-15a, miR-15b, miR16, and miR195. The 16-mer inhibitors (i.e., M-10670, M-11211, M-11213, M-11214, and M-11215) inhibit three or more family members to varying degrees.

B. In Vitro Inhibition of miR-15 Family Members by miRNA Inhibitors

Figure 8A:
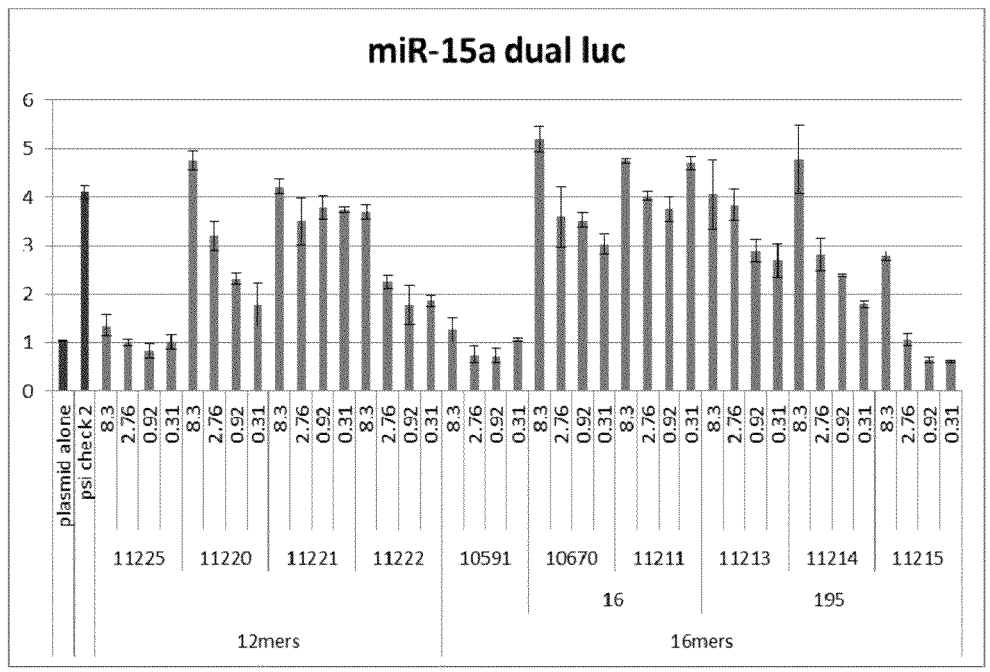
FIG. 8A shows miR-15 inhibitor efficacy measured by dual luciferase assay for miR-15a, miR-15b, miR-16, and miR-195.
Figure 8A:
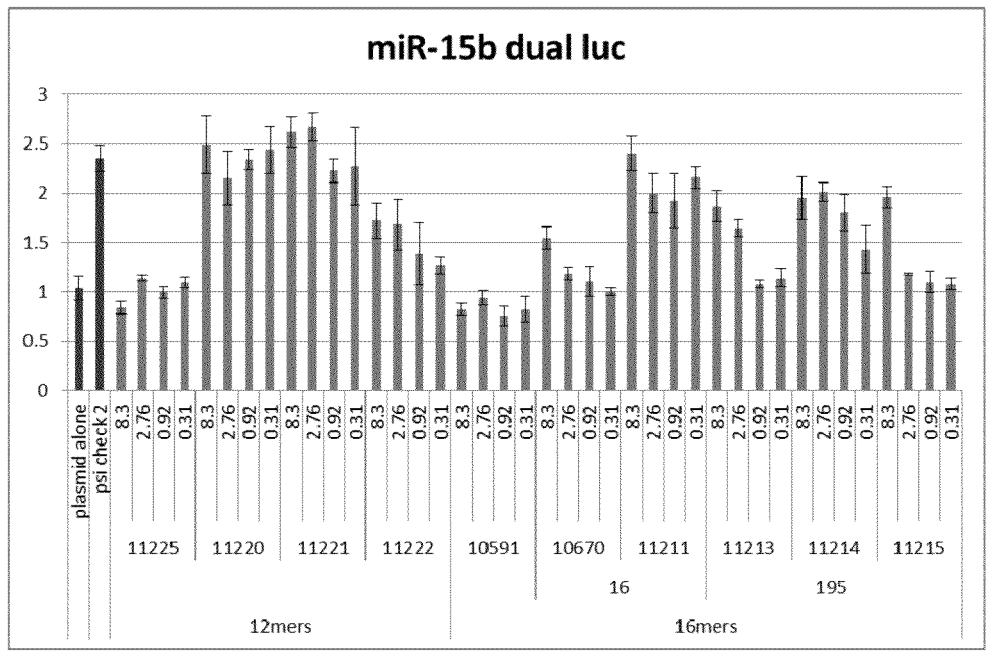
Figure 8A:
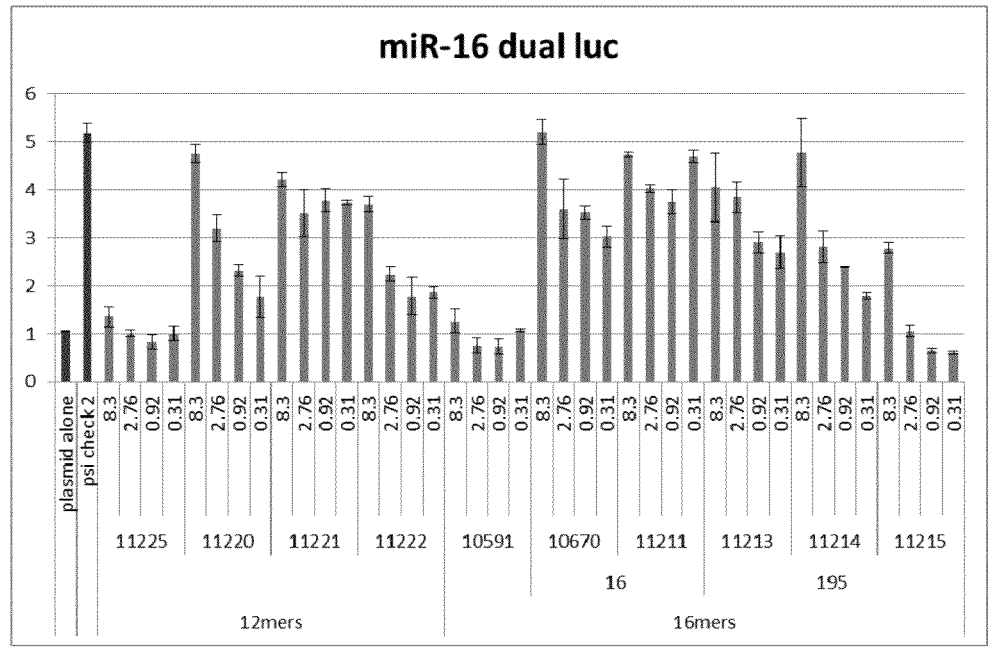
Figure 8A:
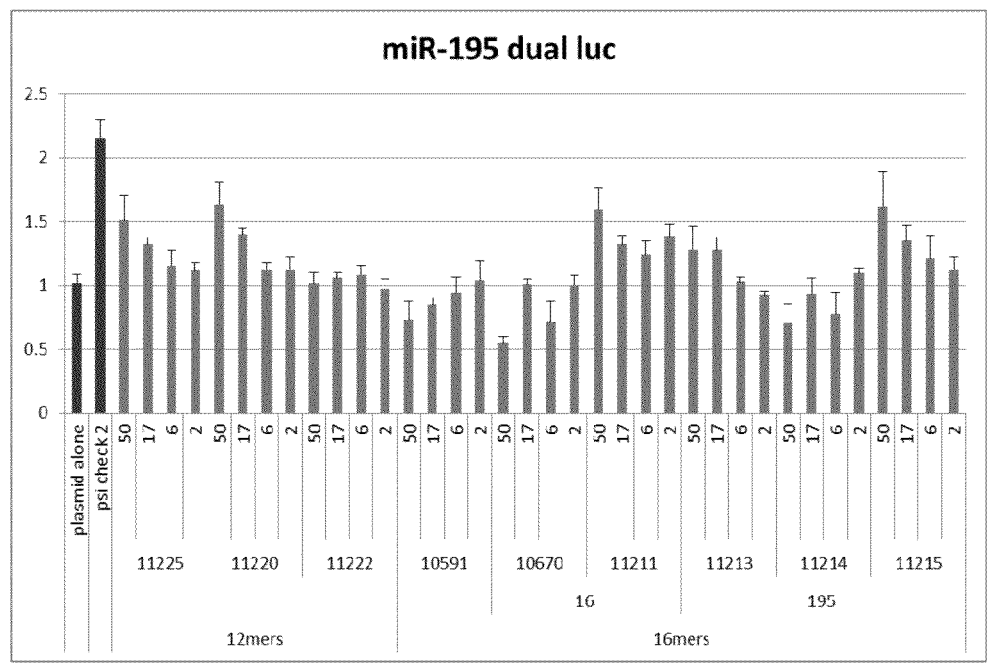

Activities of the miRNA inhibitors were tested in vitro utilizing a dual-luciferase assay. Specifically, HeLa cells were transfected with varying concentrations of a miR-15 inhibitor as well as 25 ng/well of a reporter plasmid. In particular, the miR-195 dual luciferase construct did not appear to be as sensitive as the other constructs with regard to microRNA inhibition, as demonstrated by the need to transfect inhibitor concentrations in the range of 2 to 50 nM, compared to 0.31 to 8.3 nM for the other constructs. The results (FIGS. 8A and 8B) show that the 12-mer inhibitor M-11220 is the best inhibitor tested and inhibited all four miR-15 family members. The 16-mer inhibitors (i.e., M-10670, M-11211, M-11213, M-11214, and M-11215) inhibit three or more family members to varying degrees.

Example 4

In Vivo Activity of miRNA Inhibitors Targeting the miR-15 Family

A. Dosage-Dependent De-Repression of miR-15 Targets by miRNA Inhibitors

Figure 9A:
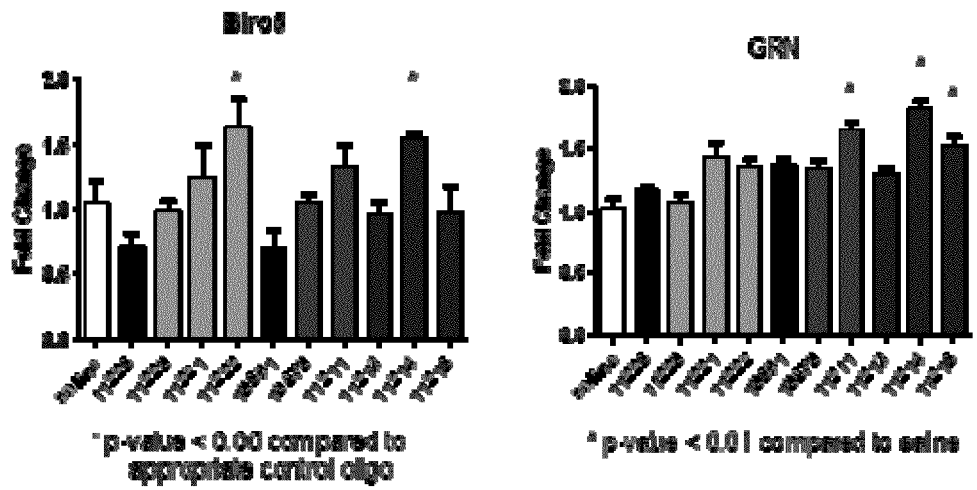
FIG. 9A shows that a therapeutic regimen of three doses (25 mg/kg per dose) of miR-15 inhibitors induces target gene de-repression in mice. Statistically significant groups with the indicated p values are indicated with an asterisk.
Figure 9A:
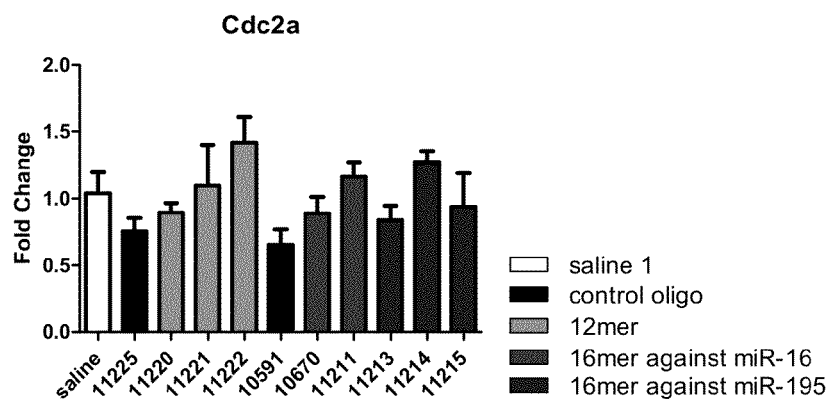
Figure 9A:
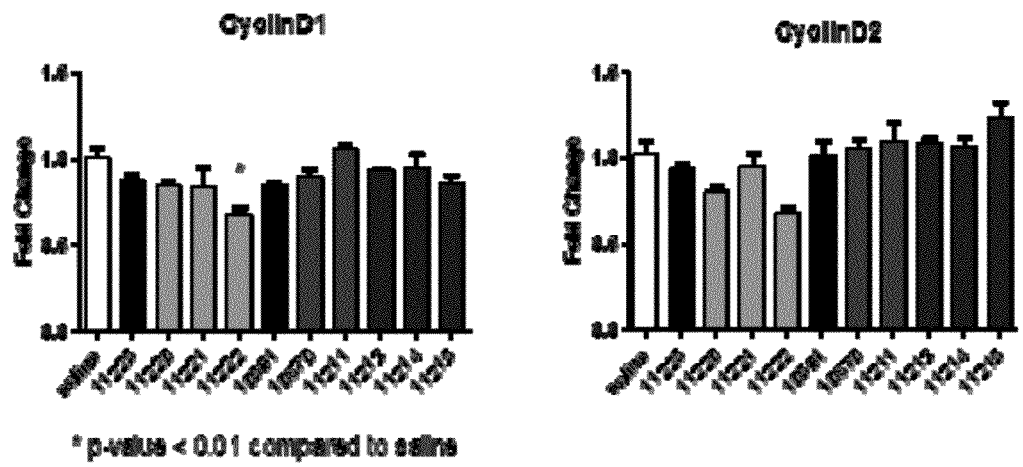
Figure 9B:
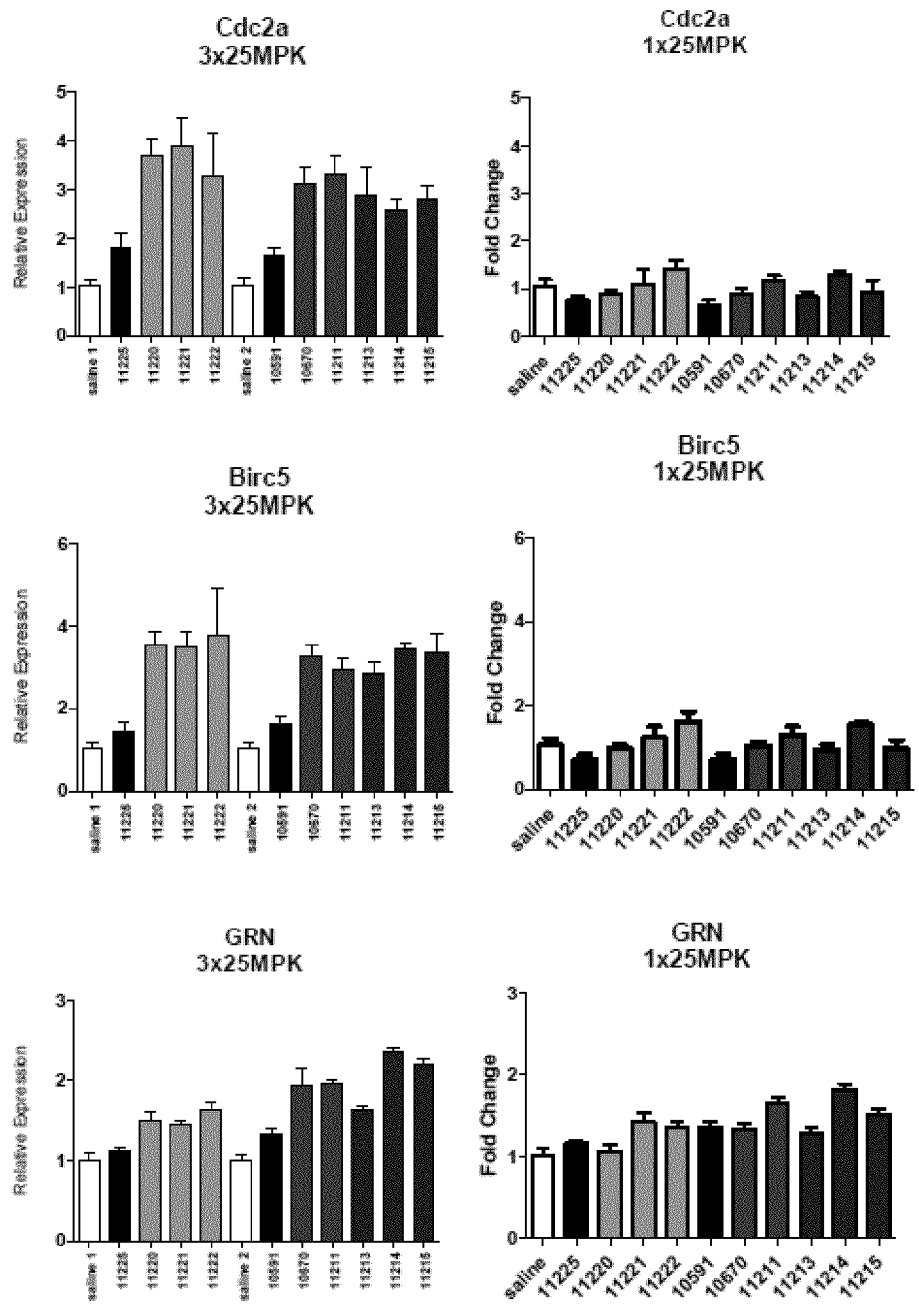
FIG. 9B shows that a therapeutic regimen of three doses (25 mg/kg per dose) of miR-15 inhibitors is more potent than a single dose regimen (25 mg/kg per dose).
Figure 9B:
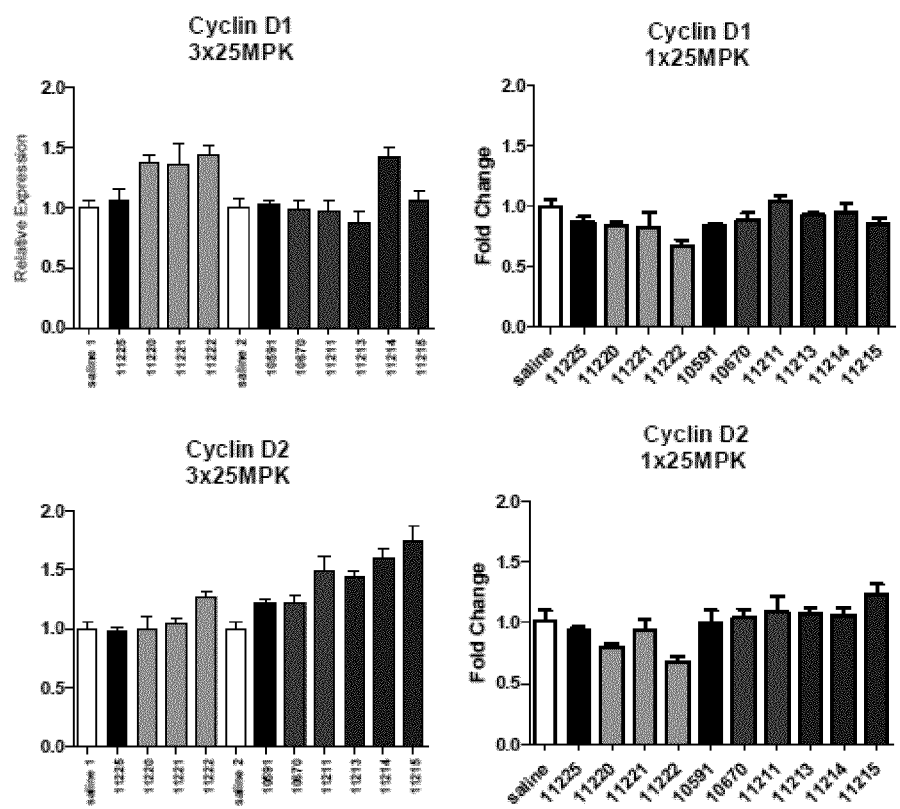

A study was performed to compare different dosage regimens of miR-15 inhibitors. Specifically, one group of mice was subcutaneously injected with inhibitors M-10670, M-11211, M-11213, M-11214, M-11215, M-11220, M-11221, or M-11222 at a dosage of 25 mg/kg. The inhibitors were administered three times over a course of three days (3×25MPK regimen) (FIG. 9A). In comparison, a second group of mice was treated with only a single dose of the miR-15 inhibitors at 25 mg/kg (1×25MPK regimen). The results (FIG. 9B) show that the 3×25MPK regimen is more potent in affecting target gene expression than the 1×25MPK regimen.

B. Kinetics of Target De-Repression by miRNA Inhibitors

Figure 10:
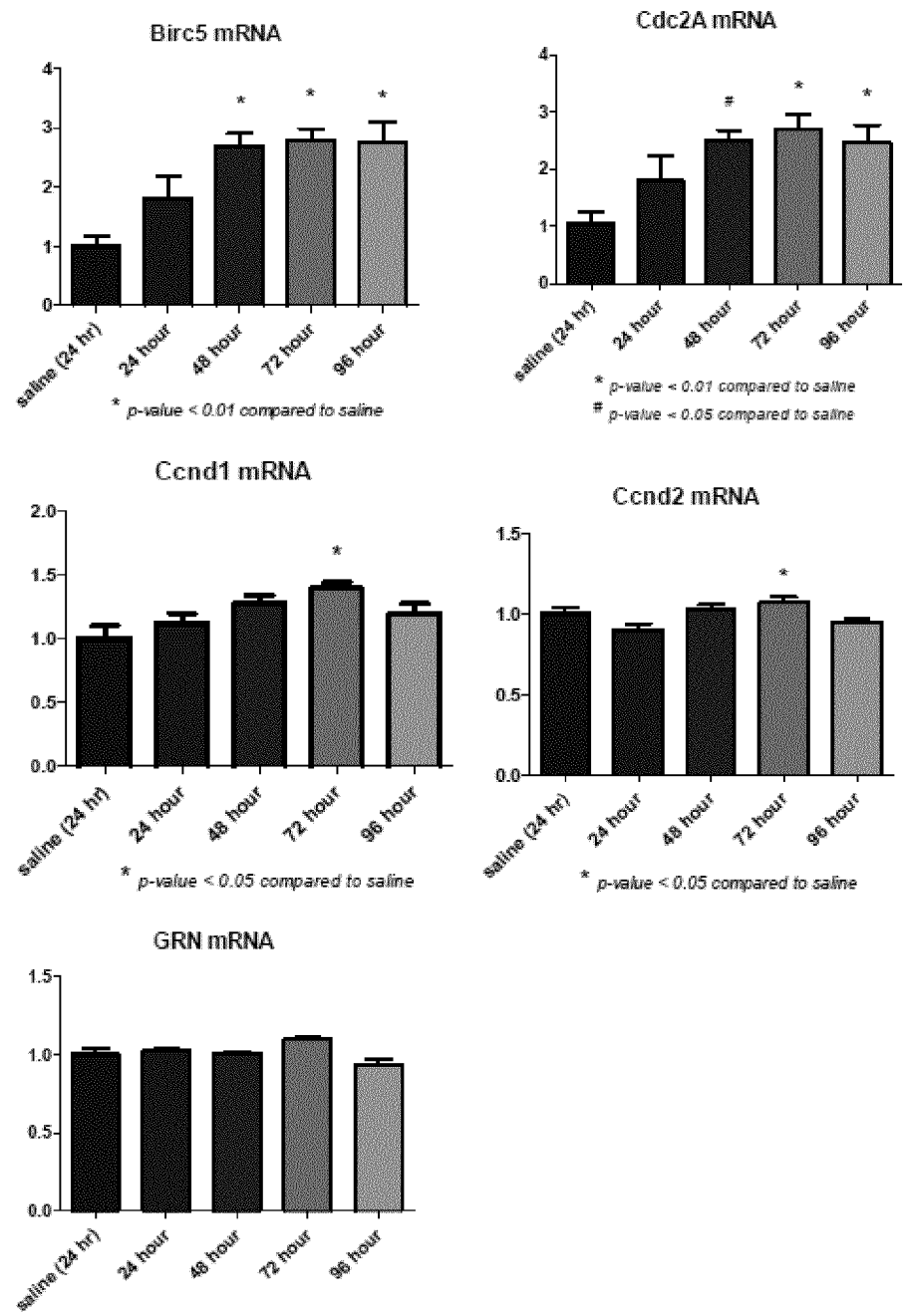
FIG. 10. Kinetics of target gene de-repression by miR-15 inhibitors.

A time-course study was performed to determine the kinetics of target de-repression by miR-15 inhibitors. Specifically, mice were subcutaneously injected with 25 mg/kg of M-11215. Only a single dose was administered. Cardiac tissue was harvested at either 24 hours, 48 hours, 72 hours, or 98 hours post injection. As shown in FIG. 10, a single dose of M-11215 elicits de-repression of target genes such as Birc5 as early as 24 hours post treatment.

C. Global and Specific Target De-Repression by miRNA Inhibitors

Figure 11:
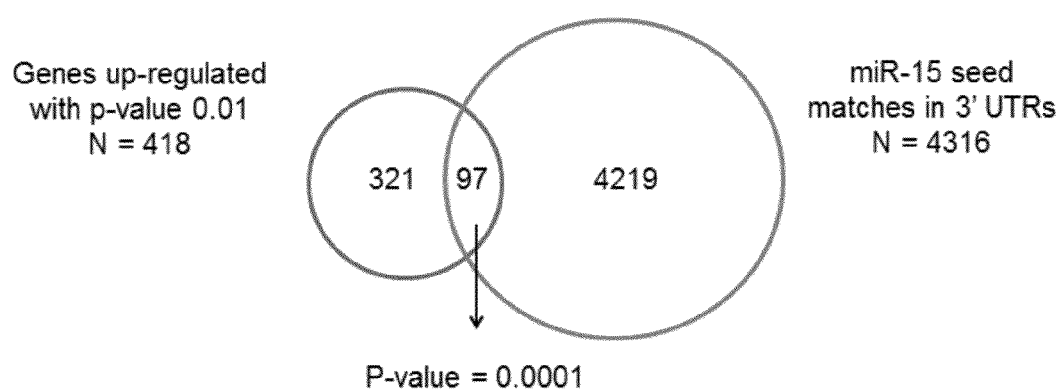
FIG. 11. Global and specific target gene de-repression by miR-15 inhibitors.

Whole genome microarray profiling was performed to determine the specificity of target de-repression by the miR-15 inhibitors. Specifically, total RNA was extracted from the cardiac tissue of M-11214 treated mice and saline treated mice. The RNA was subsequently subjected to whole genome microarray profiling. Of the genes that were upregulated when M-11214-treated cardiac total RNA was compared to saline-treated total RNA, miR-15 seed-containing genes were enriched in the upregulated gene signature (p-value: 0.01; FIG. 11). This result demonstrates that M-11214 elicits target gene de-repression that is specific to the miR-15 family.

Example 5

In Vivo Activity of miR-15 Inhibitors in Rats

Figure 12A:
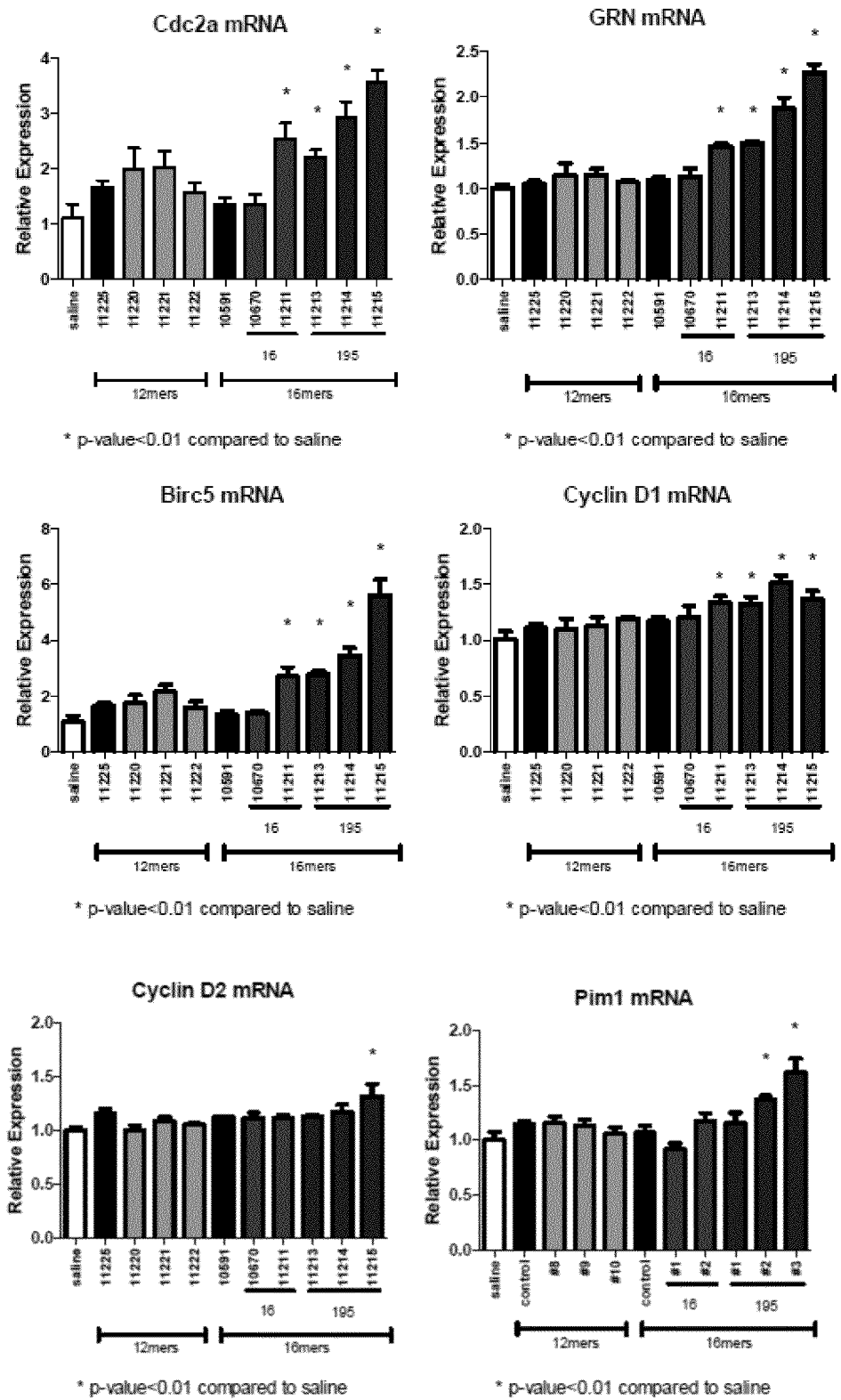
FIG. 12A shows subcutaneous injection of a single dose of miR-15 inhibitors (25 mg/kg) induces target gene de-repression four days after treatment. In rats, the 16-mer inhibitors appear to be more potent than the 12-mer inhibitors.

The in vivo activities of the miR-15 inhibitors were further tested in rats. More specifically, Sprague-Dawley rats (49 to 52 days of age) were injected with 25 mg/kg of miR-15 inhibitors including M-10670, M-11211, M-11213, M-11214, M-11215, M-11220, M-11221, or M-11222. Only a single dose was administered. Cardiac tissues were harvested at day four post injection, and target gene expression was analyzed. The results show (FIG. 12A) that 16-mer inhibitors appear to have a more potent effect on target gene expression in rats.

Results also suggest Pim1 to be a novel gene target of the miR-15 family. Overexpression of Pim1 has previously been shown to result in increased proliferative activity of cardiac progenitor cells (CPCs). CPCs are self-renewing cells that produce daughter cells which supply the heart with new myocytes and vessels, thereby stimulating myocardial regeneration. The link between miR-15 and Pim1 suggests that inhibition of miR-15 results in the production of new cardiomyocytes, which can potentially be beneficial for repairing cardiac damage.

Figure 12B:
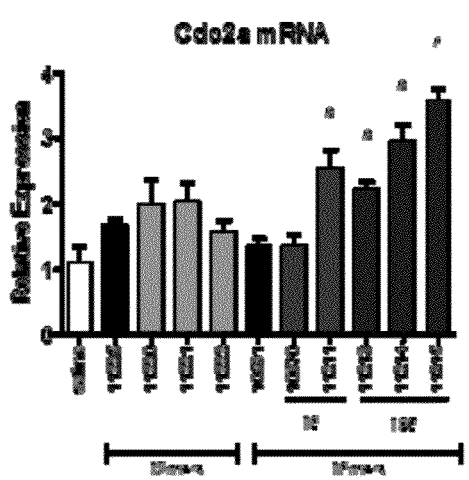
FIG. 12B compares target gene de-repression by miR-15 inhibitors in rats versus in mice at day two after treatment. The data for the graphs on the left were generated in rats, and the data for the graphs on the right were generated in mice. In general, miR-15 inhibitors appear to have a more potent effect in rats than in mice, with the exception of 12-mer inhibitors, which do not appear to be efficacious in rats.
Figure 12B:
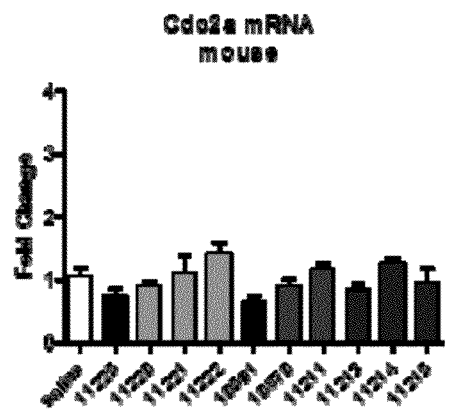
Figure 12B:
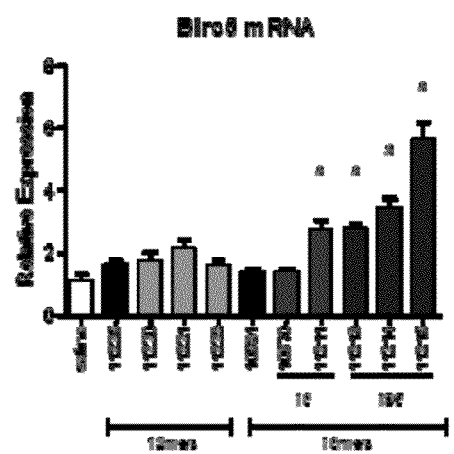
Figure 12B:
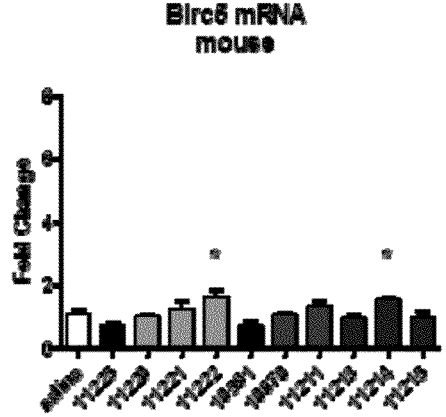
Figure 12B:
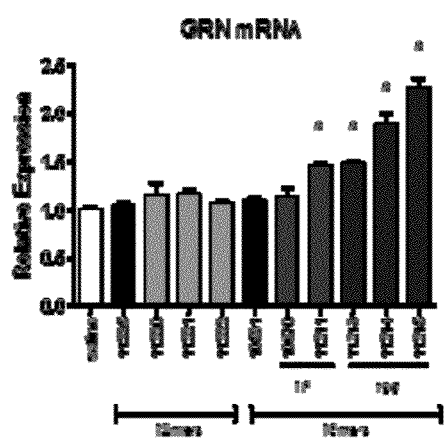
Figure 12B:
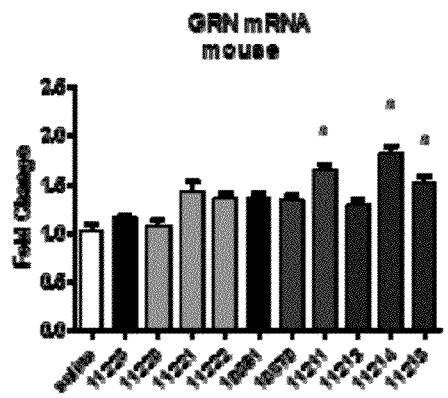
Figure 12B:
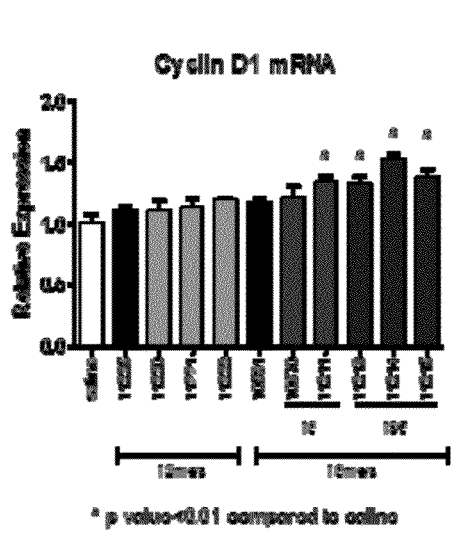
Figure 12B:
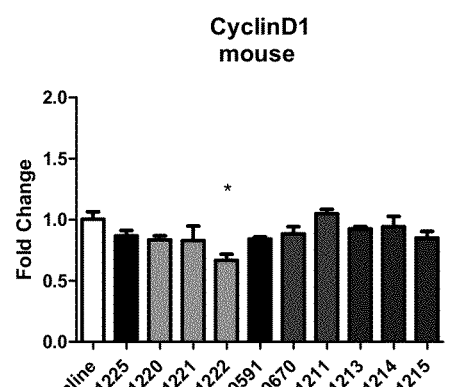
Figure 12B:
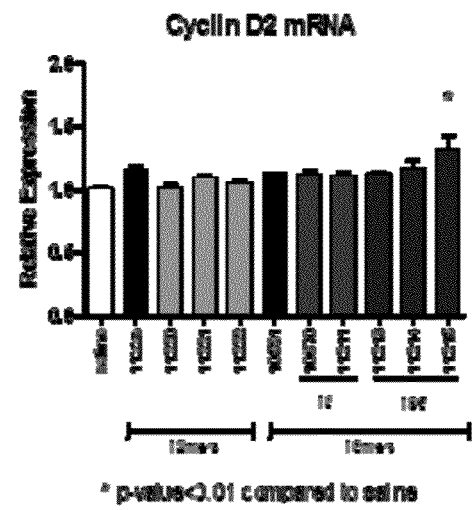
Figure 12B:
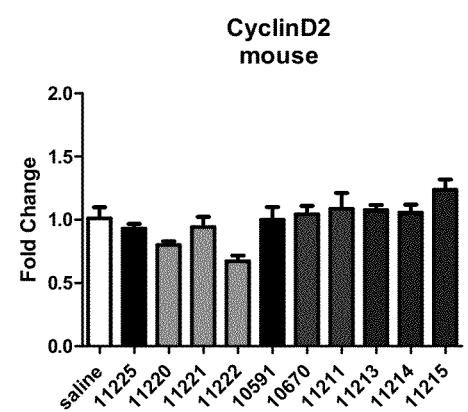

Further, a comparison study was conducted to examine the efficacy of the miR-15 inhibitors in rats and in mice. Sprague-Dawley rats were treated with miR-15 inhibitors as previously described, and cardiac tissue was analyzed for miR-15 target gene expression at 48 hours post injection. As shown in FIG. 12B, miR-15 inhibitors appear to have a more potent effect in rats than in mice with the exception of the 12-mer inhibitors which do not appear to be effective in rats.

Example 6

Figure 13:
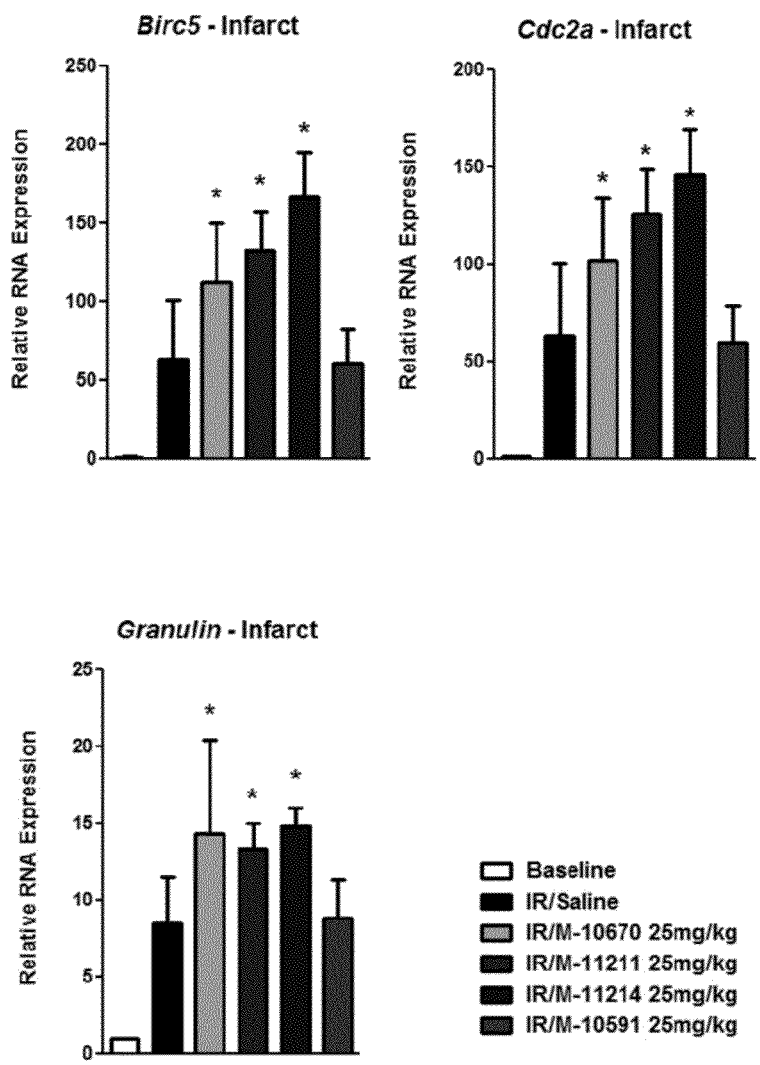
FIG. 13. Efficacy of miR-15 inhibitors on target gene de-repression in a rat stress model.

In Vivo Activity of miR-15 Inhibitors in a Rat Ischemia-Reperfusion Injury Model A. Target Gene De-Repression by miR-15 Inhibitors The in vivo activities of the miR-15 inhibitors were tested in a rat ischemia-reperfusion injury model. Specifically, in the ischemia/reperfusion model, the rats were injected intravenously with a single dose (25 mg/kg) of miR-15 inhibitors including M-10670, M-11211, M-11214, or M-10591. The rats were sacrificed at 72 hours after reperfusion, and tissues were harvested and analyzed for target gene expression (as measured by real-time PCR). As shown in FIG. 13, all miR-15 inhibitors induced significant de-repression of target genes including Birc5, Cdc2a, and Granulin when compared to non-infarcted controls (baseline).

B. Suppression of Inflammatory Markers by miR-15 Inhibitors

Figure 14:
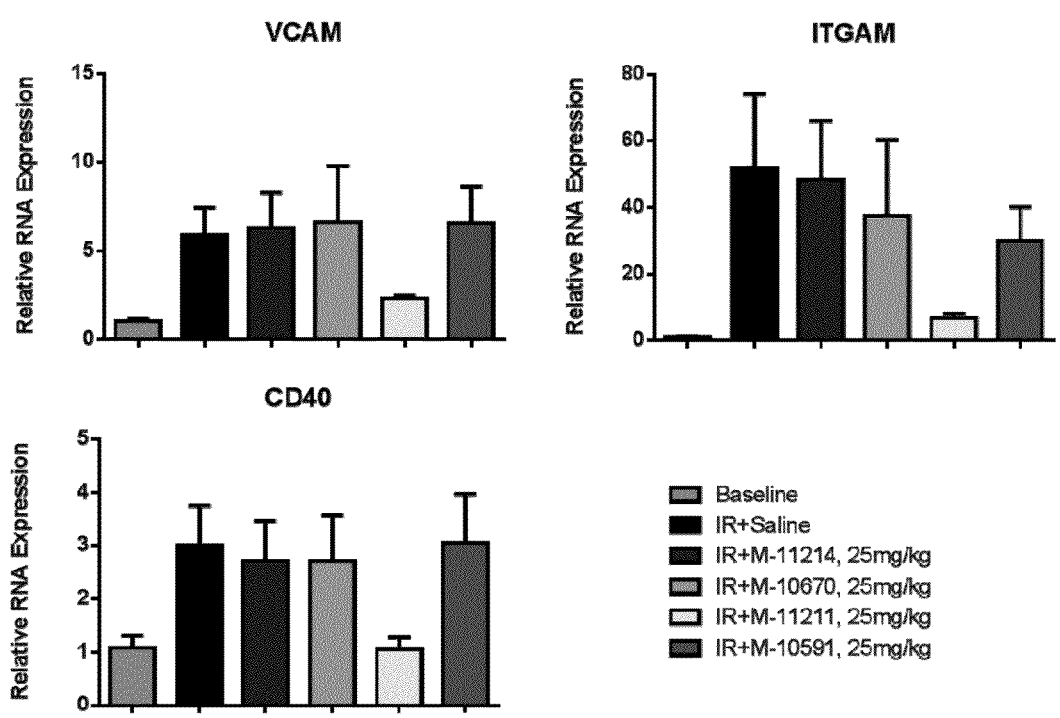
FIG. 14. Efficacy of miR-15 inhibitors on the expression of inflammatory markers in a rat stress model.

Ischemia-reperfusion injury elevated the mRNA expression of various inflammatory markers including VCAM, ITGAM, and CD40 in the border zone of the myocardial infarction. The effects of the miR-15 inhibitors on inflammatory marker expression in the border zone are shown in FIG. 14.

C. Reduction of Myocardial Infarction by miR-15 Inhibitors

Figure 15A:
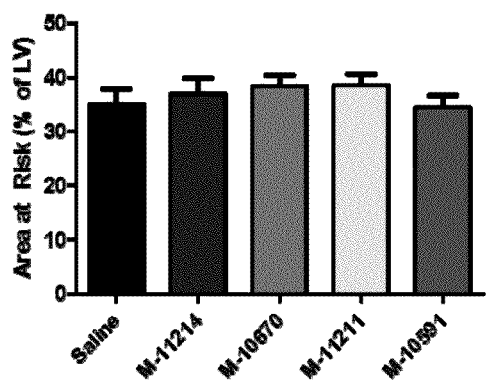
FIGS. 15A and 15B show the effects of miR-15 inhibitors on the area of risk and the size of myocardial infarction in a rat model of ischemia-reperfusion injury, respectively (n=10). Saline represents saline treated controls. M-10591 is a non-targeting control oligonucleotide.
Figure 15B:
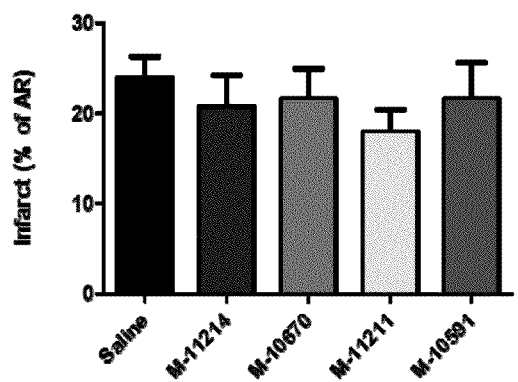

This study evaluates the effect of miR-15 inhibitors on myocardial infarction. Specifically, the area of risk as well as the size of myocardial infarction were analyzed at three days post ischemia-reperfusion injury. The effects of the miR-15 inhibitors on the area of risk and the size of myocardial infarction are shown in FIGS. 15A and 15B, respectively.

D. Improvement of Ejection Fraction by miR-15 Inhibitors

Figure 16:
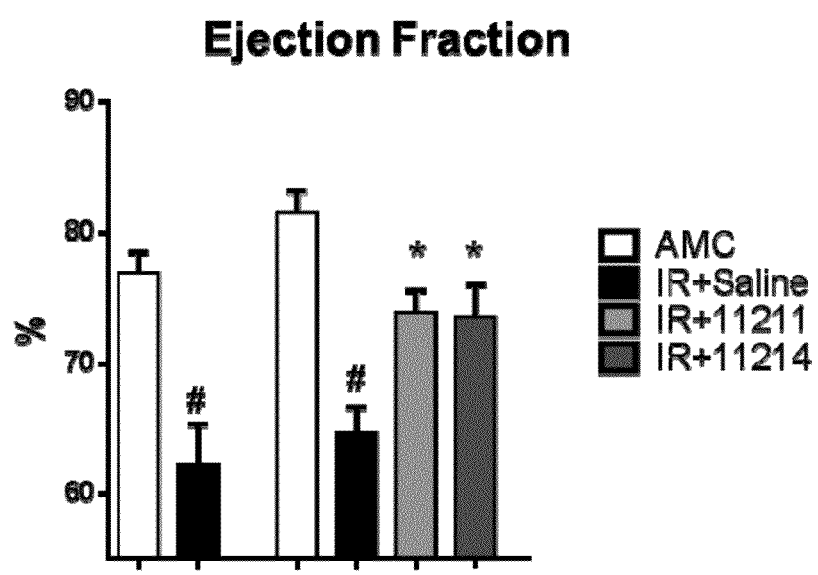
FIG. 16. Efficacy of miR-15 inhibitors (M-11211 and M-11214) on ejection fraction in a rat stress model.

This study evaluates the effects of miR-15 inhibitors on ejection fraction using a rat ischemia-reperfusion injury model. Specifically, the rats were injected intravenously with a single dose (25 mg/kg) of miR-15 inhibitors including M-11211 and M-11214 at the time of reperfusion as well as one, two, and three weeks after reperfusion (total of four injections). As shown in FIG. 16, miR-15 inhibitors significantly improved the ejection fraction at four weeks following ischemia-reperfusion injury when compared to saline treated animals.

The invention claimed is:

1. An oligonucleotide of about 1.6 nucleotides in length comprising the nucleotide sequence 5'-GTGCTGCT-3', wherein the oligonucleotide is substantially complementary to a nucleotide sequence of one or more miR-15 family members and has locked nucleotides at least at positions 1, 5, 8, 10, and 16 counting from the 5' end of the oligonucletide.

2. The oligonucleotide of claim 1, wherein said one or more miR-15 family members is selected from miR-15a, miR-15b, miR-16, miR-195, miR-424, and miR-497.

3. The oligonucleotide of claim 1, having a nucleotide sequence selected from 5'-ACCATTATGTGCTGCT-3' (SEQ ID NO. 1), 5'-ACCATGATGTGCTGCT-3' (SEQ ID NO. 2), 5'-ATATTTACGTGCTGCT-3' (SEQ ID NO. 3), and 5'-ATATTTCTGTGCTGCT-3' (SEQ ID NO. 4).

4. The oligonucleotide of claim 1, containing nine locked nucleotides and seven non-locked nucleotides.

5. The oligonucleotide of claim 1, comprising a nucleotide sequence selected from 5'-TTATGTGCTGCT-3' (SEQ ID NO. 5), 5'-TTACGTGCTGCT-3' (SEQ ID NO. 6), 5'-TTCTGTGCTGCT-3' (SEQ ID NO. 7), 5'-TTCCGTGCTGCT-3' (SEQ ID NO. 8), 5'-TGATGTGCTGCT-3' (SEQ ID NO. 9), 5'-TGACGTGCTGCT-3' (SEQ ID NO. 10), 5'-TGCTGTGCTGCT-3' (SEQ ID NO. 1), and 5'-TGCCGTGCTGCT-3' (SEQ ID NO. 12).

6. The oligonucleotide of claim 1, wherein at least one non-locked nucleotide is selected from 2' deoxy, 2'-O-methyl, 2'-O-alkyl, 2'-halo, and 2'-fluoro nucleotides.

7. The oligonucleotide of claim 1, wherein the locked nucleotides have a 2' to 4' bridge comprising an ethylene or methylene group.

8. The oligonucleotide of claim 1, having a 5' and/or 3' cap structure.

9. The oligonucleotide of claim 1, containing one or more phosphorothioate linkages.

10. The oligonucleotide of claim 9, wherein the oligonucleotide is fully phosphorothioate-linked.

11. The oligonucleotide of claim 1, having the structure of compound M-10134, M-10670, M-11206, M-11207, M-11208, M-11209, M-11210, M-11211, M-11212, M-11213, M-11214, or M-11215.

12. The oligonucleotide of claim 1, further comprising a pendent lipophilic group.

13. A pharmaceutical composition comprising an effective amount of the oligonucleotide of claim 1, or a pharmaceutically-acceptable salt thereof, and a pharmaceutically-acceptable carrier or diluent.

14. A method of reducing or inhibiting the activity of one or more miR 15 family members in a cell comprising contacting said cell with the oligonucleotide of claim 1.

15. A method of preventing or treating cardiac hypertrophy, myocardial infarction, heart failure, ischemia, or ischemia reperfusion injury in a subject, comprising administering to the subject the oligonucleotide of claim 1.

16. The oligonucleotide of claim 1, having the sequence of 5'-ATATTTACGTGCTGCT-3' (SEQ ID NO. 3), wherein the oligonucleotide has nine locked nucleotides and is fully phosphorothioate-linked.

17. The oligonucleotide of claim 1, having the sequence of 5'-ATATTTCTGTGCTGCT-3' (SEQ ID NO. 4), wherein the oligonucleotide has nine locked nucleotides and is fully phosphorothioate-linked.

* * * * *

UNITED STATES PATENT AND TRADEMARK OFFICE
CERTIFICATE OF CORRECTION

| | | |
|---|---|---|
| PATENT NO. | : 9,163,235 B2 | Page 1 of 1 |
| APPLICATION NO. | : 13/921537 | |
| DATED | : October 20, 2015 | |
| INVENTOR(S) | : Eva Van Rooij | |

It is certified that error appears in the above-identified patent and that said Letters Patent is hereby corrected as shown below:

Claims

Claim 1, line 1 (Column 37, line 15), replace "1.6" with -- 16 --.

Signed and Sealed this
Twenty-ninth Day of March, 2016

Michelle K. Lee
*Director of the United States Patent and Trademark Office*

SEQUENCE LISTING

```
<160> NUMBER OF SEQ ID NOS: 38

<210> SEQ ID NO 1
<211> LENGTH: 16
<212> TYPE: DNA
<213> ORGANISM: Artificial Sequence
<220> FEATURE:
<223> OTHER INFORMATION: chemically modified miR-15 family inhibitor
      oligonucleotide
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(16)
<223> OTHER INFORMATION: May be a locked nucleic acid residue

<400> SEQUENCE: 1
accattatgt gctgct                                                       16

<210> SEQ ID NO 2
<211> LENGTH: 16
<212> TYPE: DNA
<213> ORGANISM: Artificial Sequence
<220> FEATURE:
<223> OTHER INFORMATION: chemically modified miR-15 family inhibitor
      oligonucleotide
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(16)
<223> OTHER INFORMATION: May be a locked nucleic acid residue

<400> SEQUENCE: 2
```
accatgatgt gctgct                                                      16

<210> SEQ ID NO 3
<211> LENGTH: 16
<212> TYPE: DNA
<213> ORGANISM: Artificial Sequence
<220> FEATURE:
<223> OTHER INFORMATION: chemically modified miR-15 family inhibitor
      oligonucleotide
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(16)
<223> OTHER INFORMATION: May be a locked nucleic acid residue

<400> SEQUENCE: 3
atatttacgt gctgct                                                      16

<210> SEQ ID NO 4
<211> LENGTH: 16
<212> TYPE: DNA
<213> ORGANISM: Artificial Sequence
<220> FEATURE:
<223> OTHER INFORMATION: chemically modified miR-15 family inhibitor
      oligonucleotide
<220> FEATURE:
<221> NAME/KEY: MISC_FEATURE
<222> LOCATION: (1)..(16)
<223> OTHER INFORMATION: May be joined through phosphorothioate bonds
<220> FEATURE:
<221> NAME/KEY: MOD_RES
<222> LOCATION: (1)..(16)
<223> OTHER INFORMATION: May be a locked nucleic acid residue

<400> SEQUENCE: 4
atatttctgt gctgct                                                      16

<210> SEQ ID NO 5
<211> LENGTH: 12
<212> TYPE: DNA
<213> ORGANISM: Artificial Sequence
<220> FEATURE:
<223> OTHER INFORMATION: chemically modified miR-15 family inhibitor
      oligonucleotide
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(12)
<223> OTHER INFORMATION: May be a locked nucleic acid residue

<400> SEQUENCE: 5
ttatgtgctg ct                                                          12

<210> SEQ ID NO 6
<211> LENGTH: 12
<212> TYPE: DNA
<213> ORGANISM: Artificial Sequence
<220> FEATURE:
<223> OTHER INFORMATION: chemically modified miR-15 family inhibitor
      oligonucleotide
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES

```
<222> LOCATION: (1)..(12)
<223> OTHER INFORMATION: May be a locked nucleic acid residue

<400> SEQUENCE: 6
ttacgtgctg ct                                                              12

<210> SEQ ID NO 7
<211> LENGTH: 12
<212> TYPE: DNA
<213> ORGANISM: Artificial Sequence
<220> FEATURE:
<223> OTHER INFORMATION: chemically modified miR-15 family inhibitor
      oligonucleotide
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(12)
<223> OTHER INFORMATION: May be a locked nucleic acid residue

<400> SEQUENCE: 7
ttctgtgctg ct                                                              12

<210> SEQ ID NO 8
<211> LENGTH: 12
<212> TYPE: DNA
<213> ORGANISM: Artificial Sequence
<220> FEATURE:
<223> OTHER INFORMATION: chemically modified miR-15 family inhibitor
      oligonucleotide
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(12)
<223> OTHER INFORMATION: May be a locked nucleic acid residue

<400> SEQUENCE: 8
ttccgtgctg ct                                                              12

<210> SEQ ID NO 9
<211> LENGTH: 12
<212> TYPE: DNA
<213> ORGANISM: Artificial Sequence
<220> FEATURE:
<223> OTHER INFORMATION: chemically modified miR-15 family inhibitor
      oligonucleotide
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(12)
<223> OTHER INFORMATION: May be a locked nucleic acid residue

<400> SEQUENCE: 9
tgatgtgctg ct                                                              12

<210> SEQ ID NO 10
<211> LENGTH: 12
<212> TYPE: DNA
<213> ORGANISM: Artificial Sequence
<220> FEATURE:
<223> OTHER INFORMATION: chemically modified miR-15 family inhibitor
      oligonucleotide
<220> FEATURE:
```

```
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(12)
<223> OTHER INFORMATION: May be a locked nucleic acid residue

<400> SEQUENCE: 10
tgacgtgctg ct                                                            12

<210> SEQ ID NO 11
<211> LENGTH: 12
<212> TYPE: DNA
<213> ORGANISM: Artificial Sequence
<220> FEATURE:
<223> OTHER INFORMATION: chemically modified miR-15 family inhibitor
      oligonucleotide
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(12)
<223> OTHER INFORMATION: May be a locked nucleic acid residue

<400> SEQUENCE: 11
tgctgtgctg ct                                                            12

<210> SEQ ID NO 12
<211> LENGTH: 12
<212> TYPE: DNA
<213> ORGANISM: Artificial Sequence
<220> FEATURE:
<223> OTHER INFORMATION: chemically modified miR-15 family inhibitor
      oligonucleotide
<220> FEATURE:
<221> NAME/KEY: MISC_FEATURE
<222> LOCATION: (1)..(12)
<223> OTHER INFORMATION: May be joined through phosphorothioate bonds
<220> FEATURE:
<221> NAME/KEY: MOD_RES
<222> LOCATION: (1)..(12)
<223> OTHER INFORMATION: May be a locked nucleic acid residue

<400> SEQUENCE: 12
tgccgtgctg ct                                                            12

<210> SEQ ID NO 13
<211> LENGTH: 83
<212> TYPE: RNA
<213> ORGANISM: Homo sapiens

<400> SEQUENCE: 13
ccuuggagua aaguagcagc acauaauggu uuguggauuu ugaaaaggug caggccauau         60
ugugcugccu caaaaauaca agg                                                83

<210> SEQ ID NO 14
<211> LENGTH: 98
<212> TYPE: RNA
<213> ORGANISM: Homo sapiens

<400> SEQUENCE: 14
uugaggccuu aaaguacugu agcagcacau caugguuuac augcuacagu caagaugcga         60
aucauuauuu gcugcucuag aaauuuaagg aaauucau                                98
```

```
<210> SEQ ID NO 15
<211> LENGTH: 89
<212> TYPE: RNA
<213> ORGANISM: Homo sapiens

<400> SEQUENCE: 15
gucagcagug ccuuagcagc acguaaauau uggcguuaag auucuaaaau uaucuccagu      60
auuaacugug cugcugaagu aagguugac                                        89

<210> SEQ ID NO 16
<211> LENGTH: 81
<212> TYPE: RNA
<213> ORGANISM: Homo sapiens

<400> SEQUENCE: 16
guuccacucu agcagcacgu aaauauuggc guagugaaau auauauuaaa caccaauauu      60
acugugcugc uuuaguguga c                                                81

<210> SEQ ID NO 17
<211> LENGTH: 87
<212> TYPE: RNA
<213> ORGANISM: Homo sapiens

<400> SEQUENCE: 17
agcuucccug gcucuagcag cacagaaaua uuggcacagg gaagcgaguc ugccaauauu      60
ggcugugcug cuccaggcag gguggug                                          87

<210> SEQ ID NO 18
<211> LENGTH: 98
<212> TYPE: RNA
<213> ORGANISM: Homo sapiens

<400> SEQUENCE: 18
cgagggauua cagcagcaau ucauguuuug aaguguucua aaugguucaa aacgugaggc      60
gcugcuauac ccccucgugg ggaagguaga aggugggg                              98

<210> SEQ ID NO 19
<211> LENGTH: 112
<212> TYPE: RNA
<213> ORGANISM: Homo sapiens

<400> SEQUENCE: 19
ccaccccggu ccugcucccg ccccagcagc acacugguggu uguacggca cugugccac       60 guccaaacca cacugggug uuagagcgag ggugggggag gcaccgccga gg              112

<210> SEQ ID NO 20
<211> LENGTH: 22
<212> TYPE: RNA
<213> ORGANISM: Homo sapiens

<400> SEQUENCE: 20
uagcagcaca uaaugguuug ug                                               22

<210> SEQ ID NO 21
<211> LENGTH: 22
<212> TYPE: RNA
<213> ORGANISM: Homo sapiens

<400> SEQUENCE: 21
caggccauau ugugcugccu ca                                               22
```

```
<210> SEQ ID NO 22
<211> LENGTH: 22
<212> TYPE: RNA
<213> ORGANISM: Homo sapiens

<400> SEQUENCE: 22
uagcagcaca ucaugguuua ca                                              22

<210> SEQ ID NO 23
<211> LENGTH: 22
<212> TYPE: RNA
<213> ORGANISM: Homo sapiens

<400> SEQUENCE: 23
cgaaucauua uuugcugcuc ua                                              22

<210> SEQ ID NO 24
<211> LENGTH: 22
<212> TYPE: RNA
<213> ORGANISM: Homo sapiens

<400> SEQUENCE: 24
uagcagcacg uaaauauugg cg                                              22

<210> SEQ ID NO 25
<211> LENGTH: 22
<212> TYPE: RNA
<213> ORGANISM: Homo sapiens

<400> SEQUENCE: 25
ccaguauuaa cugugcugcu ga                                              22

<210> SEQ ID NO 26
<211> LENGTH: 22
<212> TYPE: RNA
<213> ORGANISM: Homo sapiens

<400> SEQUENCE: 26
ccaauauuac ugugcugcuu ua                                              22

<210> SEQ ID NO 27
<211> LENGTH: 21
<212> TYPE: RNA
<213> ORGANISM: Homo sapiens

<400> SEQUENCE: 27
uagcagcaca gaaauauugg c                                               21

<210> SEQ ID NO 28
<211> LENGTH: 22
<212> TYPE: RNA
<213> ORGANISM: Homo sapiens

<400> SEQUENCE: 28
ccaauauugg cugugcugcu cc                                              22

<210> SEQ ID NO 29
<211> LENGTH: 22
<212> TYPE: RNA
<213> ORGANISM: Homo sapiens

<400> SEQUENCE: 29
cagcagcaau ucauguuuug aa                                              22
```

```
<210> SEQ ID NO 30
<211> LENGTH: 21
<212> TYPE: RNA
<213> ORGANISM: Homo sapiens

<400> SEQUENCE: 30
caaaacguga ggcgcugcua u                                             21

<210> SEQ ID NO 31
<211> LENGTH: 21
<212> TYPE: RNA
<213> ORGANISM: Homo sapiens

<400> SEQUENCE: 31
cagcagcaca cugugguuug u                                             21

<210> SEQ ID NO 32
<211> LENGTH: 22
<212> TYPE: RNA
<213> ORGANISM: Homo sapiens

<400> SEQUENCE: 32
caaaccacac ugugguguua ga                                            22

<210> SEQ ID NO 33
<211> LENGTH: 17
<212> TYPE: RNA
<213> ORGANISM: Homo sapiens

<400> SEQUENCE: 33
uagcagcaca uaauggu                                                  17

<210> SEQ ID NO 34
<211> LENGTH: 17
<212> TYPE: RNA
<213> ORGANISM: Homo sapiens

<400> SEQUENCE: 34
uagcagcaca ucauggu                                                  17

<210> SEQ ID NO 35
<211> LENGTH: 17
<212> TYPE: RNA
<213> ORGANISM: Homo sapiens

<400> SEQUENCE: 35
uagcagcacg uaaauau                                                  17

<210> SEQ ID NO 36
<211> LENGTH: 17
<212> TYPE: RNA
<213> ORGANISM: Homo sapiens

<400> SEQUENCE: 36
uagcagcaca gaaauau                                                  17

<210> SEQ ID NO 37
<211> LENGTH: 17
<212> TYPE: RNA
<213> ORGANISM: Homo sapiens

<400> SEQUENCE: 37
```

```
cagcagcaau ucauguu                                                   17

<210> SEQ ID NO 38
<211> LENGTH: 17
<212> TYPE: RNA
<213> ORGANISM: Homo sapiens

<400> SEQUENCE: 38
cagcagcaca cuguggu                                                   17
```